US007964575B2

(12) United States Patent
Camby et al.

(10) Patent No.: US 7,964,575 B2
(45) Date of Patent: Jun. 21, 2011

(54) USE OF A GALECTIN-1-TARGETED RNAI-BASED APPROACH FOR THE TREATMENT OF CANCER

(75) Inventors: Isabelle Camby, Tubize (BE); Patrick Henriet, Nivelles (BE); Florence Lefranc, Sint-Pieters-Leeuw (BE); Pierre Courtoy, Brussels (BE); Robert Kiss, Sint-Pieters-Leeuw (BE)

(73) Assignees: Universite Libre de Bruxelles, Brussels (BE); Universite Catholique de Louvain, Louvain-la-Neuve (BE)

( * ) Notice: Subject to any disclaimer, the term of this patent is extended or adjusted under 35 U.S.C. 154(b) by 231 days.

(21) Appl. No.: 11/911,342

(22) PCT Filed: Mar. 9, 2006

(86) PCT No.: PCT/EP2006/002170
§ 371 (c)(1),
(2), (4) Date: Oct. 7, 2009

(87) PCT Pub. No.: WO2006/108474
PCT Pub. Date: Oct. 19, 2006

(65) Prior Publication Data
US 2010/0120891 A1    May 13, 2010

Related U.S. Application Data

(60) Provisional application No. 60/670,334, filed on Apr. 12, 2005.

(51) Int. Cl.
*A61K 31/70* (2006.01)
*C07H 21/04* (2006.01)
*C12N 15/00* (2006.01)

(52) U.S. Cl. .................. 514/44; 536/24.5; 435/320.1
(58) Field of Classification Search .................. None
See application file for complete search history.

(56) References Cited

U.S. PATENT DOCUMENTS

| 2002/0173478 | A1 | 11/2002 | Gewirtz | |
|---|---|---|---|---|
| 2003/0143732 | A1* | 7/2003 | Fosnaugh et al. | 435/325 |
| 2003/0153521 | A1* | 8/2003 | McSwiggen | 514/44 |
| 2004/0018176 | A1* | 1/2004 | Tolentino et al. | 424/93.21 |
| 2007/0178458 | A1* | 8/2007 | O'Brien et al. | 435/6 |

FOREIGN PATENT DOCUMENTS

| WO | WO 0229031 A2 * | 4/2002 |
|---|---|---|
| WO | WO 03070912 A2 * | 8/2003 |
| WO | WO 2004/012817 A | 2/2004 |

OTHER PUBLICATIONS

Camby et al. Journal of Neuropathology and Experimental Neurology 2002, vol. 61, pp. 585-596.*
Yamaoka et al. Journal of Neuroscience Research 2000, vol. 59, pp. 722-730.*
Bass Nature 2001, vol. 411, pp. 428-429.*
Vickers et al. Journal of Biological Chemistry 2003, vol. 278, pp. 7108-7118.*
Camby, I. et al. (2005) Galectin-1 knocking down in human U87 glioblastoma cells alters their gene expression pattern: Biochemical and Biophysical Research Communications 335:27-35.
Thakker, D. et al. (2004) "Neurochemical and behavioral consequences of widespread gene knockdown in the adult mouse brain by using nonviral RNA interference" PNAS 101:17270-17275.
Schiffelers, R. et al. (2004) "Cancer siRNA therapy by tumor selective delivery with ligand-targeted sterically stabilized nanoparticle" Nuclleic Acids Research 32:1-10.
Aigner, A. (2006) "Delivery systems for the direct application of siRNAs to induce RNA interference (RNAi) in vivo" Journal of Biomedicine and Biotechnology 2006:1-15.
Bartlett, D. et al. (2006) "Insights into the kinetics if siRNA-mediated gene silencing from live-cell and live-animal bioluminescent imaging" Nucleic Acids Research 34:322-333.
Filleur, S. et al. (2003) "SiRNA-mediated inhibition of vascular endothelial growth factor severely limits tumor resistance to antiangiogenic thrombospondin-1 and slows tumor vascularization and growth" Cancer Research 63:3919-3922.
Pai, S. et al. (2006) "Prospects of RNA interference therapy for cancer" Gene Therapy 13:464-477.
Rubinstein, N. et al. (2004) "Targeted inhibition of galectin-1 gene expression in tumor cells results in heightened T cell-mediated rejection: a potential mechanism of tumor-immune privilege" Cancer Cell 5:241-251.
Rabinovich, G. (2005) "Galectin-I as a potential cancer target" British Journal of Cancer 92:1188-1192.

* cited by examiner

*Primary Examiner* — Tracy Vivlemore
(74) *Attorney, Agent, or Firm* — Knobbe, Martens, Olson & Bear, LLP

(57) ABSTRACT

The present invention relates to an RNAi molecule suitable for reducing the expression of galectin-1 containing any of the sequences of SEQ ID NOs: 1-33, and preferably the sequences of SEQ ID NO: 2, 3, or 4, and to the use thereof as a medicament, or for the manufacture of a medicament for treating and/or for delaying the progression of cancer, preferably glioma, pancreatic cancer, head and neck cancer, melanoma, non-small-cell lung cancer and non-Hodgkin's lymphoma. The present invention also relates to compositions and methods for treating and for delaying the progression of cancer, preferably glioma, pancreatic cancer, head and neck cancer, melanoma, non-small-cell lung cancer and non-Hodgkin's lymphoma, for reducing the migration of tumor cells, preferably cells of glioma, pancreatic cancer, head and neck cancer, melanoma, non-small-cell lung cancer and non-Hodgkin's lymphoma, and/or for enhancing the efficacy of cancer therapies for the treatment of cancer, preferably glioma, pancreatic cancer, head and neck cancer, melanoma, non-small-cell lung cancer and non-Hodgkin's lymphoma, selected from the group comprising chemotherapy, radiation therapy, immunotherapy, and/or gene therapy.

23 Claims, 6 Drawing Sheets

Figure 1: Homo sapiens lectin, galactoside-binding, soluble, 1 (galectin 1), accession number BC020675, 556 bp

```
1    atctctctcg ggtggagtct tctgacagct ggtgcgcctg cccgggaaca tcctcctgga
61   ctcaatcatg gcttgtggtc tggtcgccag caacctgaat ctcaaacctg gagagtgcct
121  tcgagtgcga ggcgaggtgg ctcctgacgc taagagcttc gtgctgaacc tgggcaaaga
181  cagcaacaac ctgtgcctgc acttcaaccc tcgcttcaac gcccacggcg acgccaacac
241  catcgtgtgc aacagcaagg acggcgggc ctgggggacc gagcagcggg aggctgtctt
301  tcccttccag cctggaagtg ttgcagaggt gtgcatcacc ttcgaccagg ccaacctgac
361  cgtcaagctg ccagatggat acgaattcaa gttccccaac cgcctcaacc tggaggccat
421  caactacatg gcagctgacg gtgacttcaa gatcaaatgt gtggcctttg actgaaatca
481  gccagcccat ggcccccaat aaaggcagct gcctctgctc cctctgaaaa aaaaaaaaaa
541  aaaaaaaaaa aaaaaa (SEQ ID NO: 67)
```

Figure 2: Homo sapiens lectin, galactoside-binding, soluble, 1 (galectin 1), accession number BC001693, 543 bp

```
1    tcttctgaca gctggtgcgc ctgcccggga acatcctcct ggactcaatc atggcttgtg
61   gtctggtcgc cagcaacctg aatctcaaac ctggagagtg ccttcgagtg cgaggcgagg
121  tggctcctga cgctaagagc ttcgtgctga acctgggcaa agacagcaac aacctgtgcc
181  tgcacttcaa ccctcgcttc aacgcccacg gcgacgccaa caccatcgtg tgcaacagca
241  aggacggcgg ggcctggggg accgagcagc gggaggctgt ctttcccttc agcctggaa
301  gtgttgcaga ggtgtgcatc accttcgacc aggccaacct gaccgtcaag ctgccagatg
361  gatacgaatt caagttcccc aaccgcctca acctggaggc catcaactac atggcagctg
421  acggtgactt caagatcaaa tgtgtggcct ttgactgaaa tcagccagcc catggccccc
481  aataaaggca gctgcctctg ctccctctga aaaaaaaaaa aaaaaaaaaa aaaaaaaaaa
541  aaa (SEQ ID NO: 68)
```

Figure 3: Homo sapiens lectin, galactoside-binding, soluble, 1 (galectin 1), accession number NM_002305, 526 bp; with indication of the location of three putative siRNA sequences (SEQ ID NOs: 71 (underline), 72 (bold) and 73 (bold and underlined))

```
1    atctctctcg ggtggagtcc ttctgacagc tggtgcgcct gcccgggaac atcctcctgg
61   actcaatcat ggcttgtggt ctggtcgcca gcaacctgaa tctcaaacct ggagagtgcc
121  ttcgagtgcg aggcgaggtg gctcctgacg ctaagagctt cgtgctgaac ctgggcaaag
181  acagcaacaa cctgtgcctg cacttcaacc ctcgcttcaa cgcccacggc gacgccaaca
241  ccatcgtgtg caacagcaag gacggcgggg cctgggggac cgagcagcgg gaggctgtct
301  ttcccttcca gcctggaagt gttgcagagg tgtgcatcac cttcgaccag gccaacctga
361  ccgtcaagct gccagatgga tacgaattca gttccccaa ccgcctcaac ctggaggcca
481  agccagccca tggcccccaa taaaggcagc tgcctctgct ccctg (SEQ ID NO:69)
``` siRNA-1:

```
5'-GCUGCCAGAUGGAUACGAA-3'
   ||||||||||||||||||
3'-UUCGACGGUCUACCUAUGCUU-5'
``` siRNA-3:

```
5'-GUGUUGCAGAGGUGUGCAU-3'
   ||||||||||||||||||
3'-UUCACAACGUCUCCACGUU-5'
```

Figure 4

SEQUENCE LISTING

```
<160> NUMBER OF SEQ ID NOS: 104

<210> SEQ ID NO 1
<211> LENGTH: 19
<212> TYPE: RNA
<213> ORGANISM: Homo sapiens

<400> SEQUENCE: 1
aucagccagc ccauggccc                                                    19

<210> SEQ ID NO 2
<211> LENGTH: 19
<212> TYPE: RNA
<213> ORGANISM: Homo sapiens
```

```
<400> SEQUENCE: 2
gcugccagau ggauacgaa                                                  19

<210> SEQ ID NO 3
<211> LENGTH: 19
<212> TYPE: RNA
<213> ORGANISM: Homo sapiens

<400> SEQUENCE: 3
agacagcaac aaccugugc                                                  19

<210> SEQ ID NO 4
<211> LENGTH: 19
<212> TYPE: RNA
<213> ORGANISM: Homo sapiens

<400> SEQUENCE: 4
guguugcaga ggugugcau                                                  19

<210> SEQ ID NO 5
<211> LENGTH: 19
<212> TYPE: RNA
<213> ORGANISM: Homo sapiens

<400> SEQUENCE: 5
cauccuccug gacucaauc                                                  19

<210> SEQ ID NO 6
<211> LENGTH: 19
<212> TYPE: RNA
<213> ORGANISM: Homo sapiens

<400> SEQUENCE: 6
ucauggcuug uggucuggu                                                  19

<210> SEQ ID NO 7
<211> LENGTH: 19
<212> TYPE: RNA
<213> ORGANISM: Homo sapiens

<400> SEQUENCE: 7
ccugaaucuc aaaccugga                                                  19

<210> SEQ ID NO 8
<211> LENGTH: 19
<212> TYPE: RNA
<213> ORGANISM: Homo sapiens

<400> SEQUENCE: 8
ucucaaaccu ggagagugc                                                  19

<210> SEQ ID NO 9
<211> LENGTH: 19
<212> TYPE: RNA
<213> ORGANISM: Homo sapiens

<400> SEQUENCE: 9
accuggagag ugccuucga                                                  19

<210> SEQ ID NO 10
<211> LENGTH: 19
<212> TYPE: RNA
<213> ORGANISM: Homo sapiens
```

```
<400> SEQUENCE: 10
ccuggagagu gccuucgag                                                  19

<210> SEQ ID NO 11
<211> LENGTH: 19
<212> TYPE: RNA
<213> ORGANISM: Homo sapiens

<400> SEQUENCE: 11
gagcuucgug cugaaccug                                                  19

<210> SEQ ID NO 12
<211> LENGTH: 19
<212> TYPE: RNA
<213> ORGANISM: Homo sapiens

<400> SEQUENCE: 12
ccugggcaaa gacagcaac                                                  19

<210> SEQ ID NO 13
<211> LENGTH: 19
<212> TYPE: RNA
<213> ORGANISM: Homo sapiens

<400> SEQUENCE: 13
gacagcaaca accugugcc                                                  19

<210> SEQ ID NO 14
<211> LENGTH: 19
<212> TYPE: RNA
<213> ORGANISM: Homo sapiens

<400> SEQUENCE: 14
caaccugugc cugcacuuc                                                  19

<210> SEQ ID NO 15
<211> LENGTH: 19
<212> TYPE: RNA
<213> ORGANISM: Homo sapiens

<400> SEQUENCE: 15
ccugugccug cacuucaac                                                  19

<210> SEQ ID NO 16
<211> LENGTH: 19
<212> TYPE: RNA
<213> ORGANISM: Homo sapiens

<400> SEQUENCE: 16
cccucgcuuc aacgcccac                                                  19

<210> SEQ ID NO 17
<211> LENGTH: 19
<212> TYPE: RNA
<213> ORGANISM: Homo sapiens

<400> SEQUENCE: 17
cgcccacggc gacgccaac                                                  19

<210> SEQ ID NO 18
<211> LENGTH: 19
<212> TYPE: RNA
<213> ORGANISM: Homo sapiens
```

<400> SEQUENCE: 18
caccaucgug ugcaacagc                                                        19

<210> SEQ ID NO 19
<211> LENGTH: 19
<212> TYPE: RNA
<213> ORGANISM: Homo sapiens

<400> SEQUENCE: 19
cagcaaggac ggcggggcc                                                        19

<210> SEQ ID NO 20
<211> LENGTH: 19
<212> TYPE: RNA
<213> ORGANISM: Homo sapiens

<400> SEQUENCE: 20
ggacggcggg gccuggggg                                                        19

<210> SEQ ID NO 21
<211> LENGTH: 19
<212> TYPE: RNA
<213> ORGANISM: Homo sapiens

<400> SEQUENCE: 21
ccugaccguc aagcugcca                                                        19

<210> SEQ ID NO 22
<211> LENGTH: 19
<212> TYPE: RNA
<213> ORGANISM: Homo sapiens

<400> SEQUENCE: 22
uucaaguucc ccaaccgcc                                                        19

<210> SEQ ID NO 23
<211> LENGTH: 19
<212> TYPE: RNA
<213> ORGANISM: Homo sapiens

<400> SEQUENCE: 23
guuccccaac cgccucaac                                                        19

<210> SEQ ID NO 24
<211> LENGTH: 19
<212> TYPE: RNA
<213> ORGANISM: Homo sapiens

<400> SEQUENCE: 24
ccgccucaac cuggaggcc                                                        19

<210> SEQ ID NO 25
<211> LENGTH: 19
<212> TYPE: RNA
<213> ORGANISM: Homo sapiens

<400> SEQUENCE: 25
ccuggaggcc aucaacuac                                                        19

<210> SEQ ID NO 26
<211> LENGTH: 19
<212> TYPE: RNA
<213> ORGANISM: Homo sapiens

```
<400> SEQUENCE: 26
cuacauggca gcugacggu                                                    19

<210> SEQ ID NO 27
<211> LENGTH: 19
<212> TYPE: RNA
<213> ORGANISM: Homo sapiens

<400> SEQUENCE: 27
gaucaaaugu guggccuuu                                                    19

<210> SEQ ID NO 28
<211> LENGTH: 19
<212> TYPE: RNA
<213> ORGANISM: Homo sapiens

<400> SEQUENCE: 28
auguguggcc uuugacuga                                                    19

<210> SEQ ID NO 29
<211> LENGTH: 19
<212> TYPE: RNA
<213> ORGANISM: Homo sapiens

<400> SEQUENCE: 29
uguguggccu uugacugaa                                                    19

<210> SEQ ID NO 30
<211> LENGTH: 19
<212> TYPE: RNA
<213> ORGANISM: Homo sapiens

<400> SEQUENCE: 30
ucagccagcc cauggcccc                                                    19

<210> SEQ ID NO 31
<211> LENGTH: 19
<212> TYPE: RNA
<213> ORGANISM: Homo sapiens

<400> SEQUENCE: 31
uaaaggcagc ugccucugc                                                    19

<210> SEQ ID NO 32
<211> LENGTH: 19
<212> TYPE: RNA
<213> ORGANISM: Homo sapiens

<400> SEQUENCE: 32
aggcagcugc cucugcucc                                                    19

<210> SEQ ID NO 33
<211> LENGTH: 19
<212> TYPE: RNA
<213> ORGANISM: Homo sapiens

<400> SEQUENCE: 33
ggcagcugcc ucugcuccc                                                    19

<210> SEQ ID NO 34
<211> LENGTH: 53
<212> TYPE: DNA
<213> ORGANISM: Homo sapiens
<220> FEATURE:
```

<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 34
atcagccagc ccatggcccn nnnnggggcca tgggctggct gat                    53

<210> SEQ ID NO 35
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 35
gctgccagat ggatacgaan nnnnnnnnnn nnnnttcgta tccatctggc agctt        55

<210> SEQ ID NO 36
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 36
agacagcaac aacctgtgcn nnnnnnnnnn nnnngcacag gttgttgctg tcttt        55

<210> SEQ ID NO 37
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 37
gtgttgcaga ggtgtgcatn nnnnnnnnnn nnnnatgcac acctctgcaa cactt        55

<210> SEQ ID NO 38
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 38
catcctcctg gactcaatcn nnnnnnnnnn nnnngattga gtccaggagg atgtt        55

<210> SEQ ID NO 39
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times -continued

```
<400> SEQUENCE: 39
tcatggcttg tggtctggtn nnnnnnnnnn nnnnaccaga ccacaagcca tgatt          55

<210> SEQ ID NO 40
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 40
cctgaatctc aaacctggan nnnnnnnnnn nnnntccagg tttgagattc aggtt          55

<210> SEQ ID NO 41
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 41
tctcaaacct ggagagtgcn nnnnnnnnnn nnnngcactc tccaggtttg agatt          55

<210> SEQ ID NO 42
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 42
acctggagag tgccttcgan nnnnnnnnnn nnnntcgaag gcactctcca ggttt          55

<210> SEQ ID NO 43
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 43
cctggagagt gccttcgagn nnnnnnnnnn nnnnctcgaa ggcactctcc aggtt          55

<210> SEQ ID NO 44
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 44
gagcttcgtg ctgaacctgn nnnnnnnnnn nnnncaggtt cagcacgaag ctctt          55
```

```
<210> SEQ ID NO 45
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 45
cctgggcaaa gacagcaacn nnnnnnnnnn nnnngttgct gtctttgccc aggtt         55

<210> SEQ ID NO 46
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 46
gacagcaaca acctgtgccn nnnnnnnnnn nnnnggcaca ggttgttgct gtctt         55

<210> SEQ ID NO 47
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 47
caacctgtgc ctgcacttcn nnnnnnnnnn nnnngaagtg caggcacagg ttgtt         55

<210> SEQ ID NO 48
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 48
cctgtgcctg cacttcaacn nnnnnnnnnn nnnngttgaa gtgcaggcac aggtt         55

<210> SEQ ID NO 49
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 49
ccctcgcttc aacgcccacn nnnnnnnnnn nnnngtgggc gttgaagcga gggtt         55

<210> SEQ ID NO 50
<211> LENGTH: 55
<212> TYPE: DNA
<213> ORGANISM: Homo sapiens
<220> FEATURE:
```

<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 50
cgcccacggc gacgccaacn nnnnnnnnnn nnnngttggc gtcgccgtgg gcgtt    55

<210> SEQ ID NO 51
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 51
caccatcgtg tgcaacagcn nnnnnnnnnn nnnngctgtt gcacacgatg gtgtt    55

<210> SEQ ID NO 52
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 52
cagcaaggac ggcggggccn nnnnnnnnnn nnnnggcccc gccgtccttg ctgtt    55

<210> SEQ ID NO 53
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 53
ggacggcggg gcctgggggn nnnnnnnnnn nnnnccccca ggccccgccg tcctt    55

<210> SEQ ID NO 54
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 54
cctgaccgtc aagctgccan nnnnnnnnnn nnnntggcag cttgacggtc aggtt    55

<210> SEQ ID NO 55
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times -continued

```
<400> SEQUENCE: 55
ttcaagttcc ccaaccgccn nnnnnnnnnn nnnnggcggt tggggaactt gaatt        55

<210> SEQ ID NO 56
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 56
gttccccaac cgcctcaacn nnnnnnnnnn nnnngttgag gcggttgggg aactt        55

<210> SEQ ID NO 57
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 57
ccgcctcaac ctggaggccn nnnnnnnnnn nnnnggcctc aggttgagg cggtt         55

<210> SEQ ID NO 58
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 58
cctggaggcc atcaactacn nnnnnnnnnn nnnngtagt tgatggcctcc aggtt        55

<210> SEQ ID NO 59
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 59
ctacatggca gctgacggtn nnnnnnnnnn nnnnaccgtc agctgccatg tagtt        55

<210> SEQ ID NO 60
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 60
gatcaaatgt gtggcctttn nnnnnnnnnn nnnnaaaggc cacacatttg atctt        55
```

```
<210> SEQ ID NO 61
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 61
atgtgtggcc tttgactgan nnnnnnnnnn nnnntcagtc aaaggccaca cattt          55

<210> SEQ ID NO 62
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 62
tgtgtggcct ttgactgaan nnnnnnnnnn nnnnttcagt caaaggccac acatt          55

<210> SEQ ID NO 63
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 63
tcagccagcc catggcccn nnnnnnnnnn nnnnggggcc atgggctggc tgatt           55

<210> SEQ ID NO 64
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 64
taaaggcagc tgcctctgcn nnnnnnnnnn nnnngcagag gcagctgcct ttatt          55

<210> SEQ ID NO 65
<211> LENGTH: 55
<212> TYPE: DNA
<213> ORGANISM: Homo sapiens
<220> FEATURE:
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 65
aggcagctgc ctctgctccn nnnnnnnnnn nnnnggagca gaggcagctg ccttt          55

<210> SEQ ID NO 66
<211> LENGTH: 55
<212> TYPE: DNA
<213> ORGANISM: Homo sapiens
<220> FEATURE:
```

```
<221> NAME/KEY: misc_feature
<222> LOCATION: (20)..(34)
<223> OTHER INFORMATION: n = a, c, t or g; some n residues may be absent
      but they are present from 4 to 15 times

<400> SEQUENCE: 66
ggcagctgcc tctgctcccn nnnnnnnnnn nnnngggagc agaggcagct gcctt      55

<210> SEQ ID NO 67
<211> LENGTH: 556
<212> TYPE: DNA
<213> ORGANISM: Homo sapiens

<400> SEQUENCE: 67
atctctctcg ggtggagtct tctgacagct ggtgcgcctg cccgggaaca tcctcctgga      60
ctcaatcatg gcttgtggtc tggtcgccag caacctgaat ctcaaacctg gagagtgcct     120
tcgagtgcga ggcgaggtgg ctcctgacgc taagagcttc gtgctgaacc tgggcaaaga     180
cagcaacaac ctgtgcctgc acttcaaccc tcgcttcaac gccacggcg acgccaacac      240 catcgtgtgc aacagcaagg acggcggggc ctggggacc gagcagcggg aggctgtctt      300
tcccttccag cctggaagtg ttgcagaggt gtgcatcacc ttcgaccagg ccaacctgac     360
cgtcaagctg ccagatggat acgaattcaa gttccccaac cgcctcaacc tggaggccat    420
caactacatg gcagctgacg gtgacttcaa gatcaaatgt gtggcctttg actgaaatca    480
gccagcccat ggcccccaat aaaggcagct gcctctgctc cctctgaaaa aaaaaaaaa    540 aaaaaaaaaa aaaaaa                                                    556

<210> SEQ ID NO 68
<211> LENGTH: 543
<212> TYPE: DNA
<213> ORGANISM: Homo sapiens

<400> SEQUENCE: 68
tcttctgaca gctggtgcgc ctgcccggga acatcctcct ggactcaatc atggcttgtg      60
gtctggtcgc cagcaacctg aatctcaaac ctggagagtg ccttcgagtg cgaggcgagg    120
tggctcctga cgctaagagc ttcgtgctga acctgggcaa agacagcaac aacctgtgcc    180
tgcacttcaa ccctcgcttc aacgccacg gcgacgccaa caccatcgtg tgcaacagca     240
aggacggcgg ggcctggggg accgagcagc gggaggctgt ctttcccttc cagcctggaa    300
gtgttgcaga ggtgtgcatc accttcgacc aggccaacct gaccgtcaag ctgccagatg    360
gatacgaatt caagttcccc aaccgcctca acctggaggc catcaactac atggcagctg    420
acggtgactt caagatcaaa tgtgtggcct ttgactgaaa tcagccagcc catggccccc    480
aataaaggca gctgcctctg ctccctctga aaaaaaaaaa aaaaaaaaaa aaaaaaaaaa    540
aaa                                                                   543

<210> SEQ ID NO 69
<211> LENGTH: 466
<212> TYPE: DNA
<213> ORGANISM: Homo sapiens

<400> SEQUENCE: 69
atctctctcg ggtggagtcc ttctgacagc tggtgcgcct gcccgggaac atcctcctgg      60
actcaatcat ggcttgtggt ctggtcgcca gcaacctgaa tctcaaacct ggagagtgcc    120
ttcgagtgcg aggcgaggtg gctcctgacg ctaagagctt cgtgctgaac ctgggcaaag    180
acagcaacaa cctgtgcctg cacttcaacc ctcgcttcaa cgcccacggc gacgccaaca    240
```

-continued

```
ccatcgtgtg caacagcaag gacggcgggg cctgggggac cgagcagcgg gaggctgtct    300
ttcccttcca gcctggaagt gttgcagagg tgtgcatcac cttcgaccag gccaacctga    360
ccgtcaagct gccagatgga tacgaattca agttccccaa ccgcctcaac ctggaggcca    420
agccagccca tggcccccaa taaaggcagc tgcctctgct cccctg                   466
```

<210> SEQ ID NO 70
<211> LENGTH: 21
<212> TYPE: DNA
<213> ORGANISM: Homo sapiens

<400> SEQUENCE: 70

```
aaatcagcca gcccatggcc c                                               21
```

<210> SEQ ID NO 71
<211> LENGTH: 21
<212> TYPE: DNA
<213> ORGANISM: Homo sapiens

<400> SEQUENCE: 71

```
aagctgccag atggatacga a                                               21
```

<210> SEQ ID NO 72
<211> LENGTH: 21
<212> TYPE: DNA
<213> ORGANISM: Homo sapiens

<400> SEQUENCE: 72

```
aaagacagca acaacctgtg c                                               21
```

<210> SEQ ID NO 73
<211> LENGTH: 21
<212> TYPE: DNA
<213> ORGANISM: Homo sapiens

<400> SEQUENCE: 73

```
aagtgttgca gaggtgtgca t                                               21
```

<210> SEQ ID NO 74
<211> LENGTH: 21
<212> TYPE: DNA
<213> ORGANISM: Homo sapiens

<400> SEQUENCE: 74

```
aacatcctcc tggactcaat c                                               21
```

<210> SEQ ID NO 75
<211> LENGTH: 21
<212> TYPE: DNA
<213> ORGANISM: Homo sapiens

<400> SEQUENCE: 75

```
aatcatggct tgtggtctgg t                                               21
```

<210> SEQ ID NO 76
<211> LENGTH: 21
<212> TYPE: DNA
<213> ORGANISM: Homo sapiens

<400> SEQUENCE: 76

```
aacctgaatc tcaaacctgg a                                               21
```

```
<210> SEQ ID NO 77
<211> LENGTH: 21
<212> TYPE: DNA
<213> ORGANISM: Homo sapiens

<400> SEQUENCE: 77
aatctcaaac ctggagagtg c                                              21

<210> SEQ ID NO 78
<211> LENGTH: 21
<212> TYPE: DNA
<213> ORGANISM: Homo sapiens

<400> SEQUENCE: 78
aaacctggag agtgccttcg a                                              21

<210> SEQ ID NO 79
<211> LENGTH: 21
<212> TYPE: DNA
<213> ORGANISM: Homo sapiens

<400> SEQUENCE: 79
aacctggaga gtgccttcga g                                              21

<210> SEQ ID NO 80
<211> LENGTH: 21
<212> TYPE: DNA
<213> ORGANISM: Homo sapiens

<400> SEQUENCE: 80
aagagcttcg tgctgaacct g                                              21

<210> SEQ ID NO 81
<211> LENGTH: 21
<212> TYPE: DNA
<213> ORGANISM: Homo sapiens

<400> SEQUENCE: 81
aacctgggca agacagcaa c                                               21

<210> SEQ ID NO 82
<211> LENGTH: 21
<212> TYPE: DNA
<213> ORGANISM: Homo sapiens

<400> SEQUENCE: 82
aagacagcaa caacctgtgc c                                              21

<210> SEQ ID NO 83
<211> LENGTH: 21
<212> TYPE: DNA
<213> ORGANISM: Homo sapiens

<400> SEQUENCE: 83
aacaacctgt gcctgcactt c                                              21

<210> SEQ ID NO 84
<211> LENGTH: 21
<212> TYPE: DNA
<213> ORGANISM: Homo sapiens

<400> SEQUENCE: 84
aacctgtgcc tgcacttcaa c                                              21
```

```
<210> SEQ ID NO 85
<211> LENGTH: 21
<212> TYPE: DNA
<213> ORGANISM: Homo sapiens

<400> SEQUENCE: 85
aaccctcgct tcaacgccca c                                              21

<210> SEQ ID NO 86
<211> LENGTH: 21
<212> TYPE: DNA
<213> ORGANISM: Homo sapiens

<400> SEQUENCE: 86
aacgcccacg gcgacgccaa c                                              21

<210> SEQ ID NO 87
<211> LENGTH: 21
<212> TYPE: DNA
<213> ORGANISM: Homo sapiens

<400> SEQUENCE: 87
aacaccatcg tgtgcaacag c                                              21

<210> SEQ ID NO 88
<211> LENGTH: 21
<212> TYPE: DNA
<213> ORGANISM: Homo sapiens

<400> SEQUENCE: 88
aacagcaagg acggcggggc c                                              21

<210> SEQ ID NO 89
<211> LENGTH: 21
<212> TYPE: DNA
<213> ORGANISM: Homo sapiens

<400> SEQUENCE: 89
aaggacggcg gggcctgggg g                                              21

<210> SEQ ID NO 90
<211> LENGTH: 21
<212> TYPE: DNA
<213> ORGANISM: Homo sapiens

<400> SEQUENCE: 90
aacctgaccg tcaagctgcc a                                              21

<210> SEQ ID NO 91
<211> LENGTH: 21
<212> TYPE: DNA
<213> ORGANISM: Homo sapiens

<400> SEQUENCE: 91
aattcaagtt ccccaaccgc c                                              21

<210> SEQ ID NO 92
<211> LENGTH: 21
<212> TYPE: DNA
<213> ORGANISM: Homo sapiens

<400> SEQUENCE: 92
aagttcccca accgcctcaa c                                              21
```

```
<210> SEQ ID NO 93
<211> LENGTH: 21
<212> TYPE: DNA
<213> ORGANISM: Homo sapiens

<400> SEQUENCE: 93
aaccgcctca acctggaggc c                                              21

<210> SEQ ID NO 94
<211> LENGTH: 21
<212> TYPE: DNA
<213> ORGANISM: Homo sapiens

<400> SEQUENCE: 94
aacctggagg ccatcaacta c                                              21

<210> SEQ ID NO 95
<211> LENGTH: 21
<212> TYPE: DNA
<213> ORGANISM: Homo sapiens

<400> SEQUENCE: 95
aactacatgg cagctgacgg t                                              21

<210> SEQ ID NO 96
<211> LENGTH: 21
<212> TYPE: DNA
<213> ORGANISM: Homo sapiens

<400> SEQUENCE: 96
aagatcaaat gtgtggcctt t                                              21

<210> SEQ ID NO 97
<211> LENGTH: 21
<212> TYPE: DNA
<213> ORGANISM: Homo sapiens

<400> SEQUENCE: 97
aaatgtgtgg cctttgactg a                                              21

<210> SEQ ID NO 98
<211> LENGTH: 21
<212> TYPE: DNA
<213> ORGANISM: Homo sapiens

<400> SEQUENCE: 98
aatgtgtggc ctttgactga a                                              21

<210> SEQ ID NO 99
<211> LENGTH: 21
<212> TYPE: DNA
<213> ORGANISM: Homo sapiens

<400> SEQUENCE: 99
aatcagccag cccatggccc c                                              21

<210> SEQ ID NO 100
<211> LENGTH: 21
<212> TYPE: DNA
<213> ORGANISM: Homo sapiens

<400> SEQUENCE: 100
aataaaggca gctgcctctg c                                              21
```

```
<210> SEQ ID NO 101
<211> LENGTH: 21
<212> TYPE: DNA
<213> ORGANISM: Homo sapiens

<400> SEQUENCE: 101
aaaggcagct gcctctgctc c                                             21

<210> SEQ ID NO 102
<211> LENGTH: 21
<212> TYPE: DNA
<213> ORGANISM: Homo sapiens

<400> SEQUENCE: 102
aaggcagctg cctctgctcc c                                             21

<210> SEQ ID NO 103
<211> LENGTH: 21
<212> TYPE: RNA
<213> ORGANISM: Homo sapiens

<400> SEQUENCE: 103
uucguaucca ucuggcagcu u                                             21

<210> SEQ ID NO 104
<211> LENGTH: 21
<212> TYPE: RNA
<213> ORGANISM: Homo sapiens

<400> SEQUENCE: 104
uugcacaccu cugcaacacu u                                             21
```

USE OF A GALECTIN-1-TARGETED RNAI-BASED APPROACH FOR THE TREATMENT OF CANCER

This application is the U.S. National Phase under 35 U.S.C. §371 of International Application PCT/EP2006/002170, filed Mar. 9, 2006, which claims priority to U.S. Patent Application No. 60/670,334, filed Apr. 12, 2005.

FIELD OF THE INVENTION

The present invention relates in general to the use of RNAi technology for gene silencing of a target gene (galectin-1) involved in tumor progression. More in particular the present invention relates to the use of RNAi molecules for treating cancer, such as glioma, pancreatic cancer, head and neck cancer, melanoma, non-small-cell lung cancer and non-Hodgkin's lymphoma.

BACKGROUND OF THE INVENTION

The development of novel anti-cancer agents since 2000 includes about 1200 projects from in vivo lead optimisation, through pre-clinical phases, to Phase III clinical trials (Expert Opinion Emerging Drugs 6, 2001). Of these 1200 projects, less than 15% are under Phase I to Phase III clinical trials. Cytotoxic and cytostatic drugs and signaling pathway inhibitors are the two largest groups under development. Together with anti-angiogenic compounds and biologicals, e.g., monoclonal antibodies, they represent about 70% of anti-cancer drugs assayed in clinical phases since 2000. Further 19% of anti-cancer drugs under clinical trials belong to hormone therapy, cell cycle inhibitors, chemoprotective and histone deacetylase inhibitors. Compared to the above, only 3 anti-migratory (anti-metastatic) compounds entered clinical trials, i.e., 2% of those under clinical trials in oncology.

Despite the availability of more efficacious cytotoxic and cytostatic drugs and monoclonal antibodies that target cancer cells, the treatment of patients in advanced and/or metastatic disease remains highly unsatisfactory. The use of inhibitors of signaling pathways is further complicated because such pathways are not all activated at the same time during progression of a cancer. Rather, particular inhibitors need to be applied only when the corresponding target is present in the tumor tissue. Therefore, individual patients need to undergo molecular profiling of their tumors before any treatment, which decreases the efficiency and cost-effectiveness of the treatment, and introduces a delay before effective treatment can be started.

In view of the above, there remains a need for novel therapeutic approaches to combat cancer. New cellular targets are needed, as well as therapeutic molecules which can efficiently impinge on these targets. The cellular targets may preferably be involved in different cancers and may play a role in various disease mechanisms, such as, e.g., in migration of cancer cells and metastasis.

Galectins, originally named as galactose-specific lectins, is a family of 15 members in mammals. Each member of this family is expressed in a restricted set of normal and neoplastic tissues and is associated with distinct biological functions (Danguy et al. 2002). Galectins form homodimers or oligomers that can readily bridge N- and O-glycans as well as glycolipids present on cell surfaces with similar glycans in the ECM. In addition, cross-linking of β-galactoside-containing plasma membrane glycoconjugates modulates cell signaling, adhesion and survival. Although most galectins have been described as extracellular actors, intracellular functions have also been described. They have been found to play a number of important roles in biological processes including cellular processes involving cancers. As such, the role of galectins is very strongly tied to cancer and other proliferative diseases.

More specifically, the inventors contemplate that galectin-1 expression or over-expression in tumors or in tissues surrounding the tumors can be considered as a sign of malignant progression of the tumor and is often associated with poor prognosis for patients, often related to the dissemination of tumor cells at distance (metastasis) or in the surrounding normal tissue and to tumor immune-escape.

The inventors find that galectin-1 expression or over-expression may play particularly important role in non-small-cell-lung cancer (NSCLC), non-Hodgkin's (NH) lymphoma, pancreatic cancer, head & neck cancer, melanoma and glioma (brain tumors). These six cancer types may account for about 19.8% or more of all cancers encountered in female patients and about 37.2% or more of all cancers encountered in male patients. Hence, the number of female and male patients benefiting from an efficient targeting of these cancer types may be about 1,261,000 new cancer patients per year.

For example, galectin-1 is over-expressed in pancreatic ductal adenocarcinomas (Grutzmann et al. 2004; Shen et al. 2004) as compared to normal tissue and pancreatitis, a fact that relates to the level of differentiation of tumor cells (Berberat et al. 2001). Pancreatic stellate cells play a key role in the development of pancreatic fibrosis, a pathological feature of chronic pancreatitis and pancreatic cancer. Fritzner et al. 2005, showed that activation of rat pancreatic stellate cells is associated with increased expression of galectin-1 that modulates pancreatic stellate cell functions.

Galectin-1 expression has been demonstrated in head and neck squamous cell carcinomas (HNSCC). It is expressed within the invasive compartment of tumors (Gillenwater 1996) in relation with aggressiveness (Choufani et al. 1999).

Patients with non-small-cell lung cancer (NSCLC) are often positive for galectin-1 expression, among which adenocarcinomas figure prominently. The galectin-1 expression tends to increase with the progression of the malignancy and is an unfavorable independent prognostic factor that may relate to the proliferative activity of tumor cells (Szoke T et al. 2005; Gabius et al. 2002).

Recombinant galectin-1 added extracellularly to melanoma cells induces a dose-dependent increase of cell adhesion on laminin or fibronectin (van den Brule et al. 1995) and cell aggregation though interaction with glycoprotein 90K/MAC-2BP (Tinari N et al. 2001). The immunomodulatory effects of galectin-1 and the correlation between galectin-1 expression in cancer cells and the aggressiveness of these tumors (Rabinovich et al. 2002) make the inventors hypothesize that tumor cells may impair T-cell effector functions through secretion of galectin-1 and that this mechanism may contribute in tilting the balance towards an immunosuppressive environment at the tumor site. Rubinstein et al. 2004 advocated a link between galectin-1-mediated immuno-regulation and its contribution to tumor-immune escape. Blockade of the inhibitory effects of galectin-1 within melanoma tissue resulted in reduced tumor mass and stimulated the generation of a tumor-specific T-cell response in vivo. This supports the idea that galectin-1 may contribute to immune privilege of tumor by modulating survival or polarization of effector T cells, and suggest a potential molecular target for manipulation of T-cell apoptosis with potential implication in the therapeutic of cancer.

While the vessel walls of normal lymphoid tissues do not express galectin-1, the blood vessel walls in lymphomas express galectin-1 in relation with vascular density (D'Haene et al. 2005). Sezary cells, the malignant T cells in cutaneous T cell lymphoma (Sezary syndrome or mycosis fungoides) resist a variety of apoptosis—inducing agents, including galectin-1 induced apoptosis because of the loss of CD7 expression and altered cellular glycosylation. Recent evidence also indicates that galectin-1 (dGal-1) can induce the exposure of phosphatidylserine (an early apoptotic marker involved in the phagocytosis of apoptotic cells) on the plasma membrane of the human T leukemia MOLT-4 cells as well as on promyelocytic cell line and activated neutrophils, but that this does not result in cell death but prepares cells for phagocytic removal.

Galectin-1 has been reported to be the most important member of the galectin family in physiological brain processes (Danguy et al. 2002, Camby et al. 2001, Zanetta, 1998). The present invention is at least partly based on the finding of a direct implication of galectin-1 in the development of malignancy of human gliomas.

In patients bearing human glial tumors, the levels and patterns of expression of galectin-1 correlate with the development of malignancy (Camby et al. 2001). In a recent survey of clinical samples of high-grade astrocytic tumors, it was noticed that a low level of expression of galectin-1 in human malignant gliomas was associated with unusually long survival of such malignant glioma patients (Camby et al. 2001). Conversely, elevated levels of galectin-1 expression have been observed for highly invasive tumoral astrocytes, both in human surgical samples and animal models (Camby et al. 2001).

While increasing levels in galectin-1 expression correlate with malignancy development in human gliomas, such development of malignancy in human gliomas is associated with a marked decrease in galectin-3 expression (Camby et al. 2001). These data indicate different roles for galectin-1 and galectin-3 in the development of glioma malignancy. Therefore, the use of an anti-galectin-3 strategy for therapeutic purpose to combat cancer in general cannot be extrapolated to glioma in particular.

A direct involvement of galectin-1 in the aggressive behavior of malignant gliomas has been reported (Camby et al. 2002; Rorive et al. 2001, Gunnersen et al. 2000, Yamaoka et al. 2000).

For instance, the applicant has shown that in vitro, the addition of galectin-1 into the culture medium of U87 human glioblastoma cells markedly increased their migration capabilities (Camby et al. 2002, Rorive et al. 2001). These effects were associated with actin cytoskeleton reorganization and with increased expression in the small GTPase, RhoA (Camby et al. 2002). Conversely, human U87 glioblastoma cells constitutively expressing reduced levels of galectin-1 (U87/G1⁻) by means of stable transfection of an expression vector for antisense mRNA of galectin-1 were engineered. In vivo, intracranial grafting of U87/G1⁻ cells into nude mice led to much longer survival in comparison with mice grafted with control cells (Camby et al. 2002). In vitro, U87/G1⁻ cells were much less motile than parental (wt) and mock-transfected cells (Camby et al. 2002). Long-term deficiency in galectin-1 expression in these cells did not modify cell growth properties but impaired cell adhesion and invasiveness in Boyden chambers, and decreased expression and secretion and activity of matrix metalloproteinase-2. Matrix metalloproteinases-2 exerts marked roles in the development of malignancy of human gliomas (Rao 2003). The decrease in the levels of expression and secretion of galectin-1 in tumor astrocytes decreases the levels of expression and secretion of MMP-2 in these tumor astrocytes, a feature that will in turn decrease the capacity of tumor astrocytes to invade the brain parenchyma (Camby et al., 2002).

In order to further orient the study of the molecular mechanisms whereby galectin-1 promotes adhesion, motility and invasion of tumor astrocytes, the effect of stable transfection with antisense galectin-1 vector to mock-transfected and wild-type cells was also compared by cDNA microarray analysis. The expression of 91 genes (among 631 genes potentially involved in cancer) was increased by at least 2-fold. Confirmation of increased protein level was provided by immunocytochemistry for $p21^{waf/cip1}$, cullin-2, p53, $\alpha9\beta1$ integrin, ADAM-15 and MAP-2. Major differences in the expression pattern of $\alpha9\beta1$ integrin and ADAM-15 proteins were also observed.

The use of galectin inhibitors for treating cancer in general has been reported. For instance, the use of an anti-galectin-4 or anti-galectin-9 therapeutic approach to combat certain types of cancers has been suggested. However, the present invention does not target galectin-4 or galectin-9.

US 2003/0109464 describes methods for inhibiting the growth and/or metastasis of a breast tumor in a subject by administering a therapeutic compound that binds and/or inhibits the activity of GAL-1 or GAL-4. The therapeutic compounds are amino acids or polypeptides coupled to one or more sugars. In some cases, parts of the GAL-1 and GAL-1 proteins themselves (e.g. parts of the binding domains) are used as therapeutic compounds, in other cases, non-GAL proteins (e.g. glycoamines) are used as therapeutic agents. The described approach is directed to the treatment of breast cancer and is not suitable or effective for the treatment of the above cancers, e.g., glioma, non-Hodgkin's lymphomas, non-small-cell-lung cancers, head & neck cancers, melanomas and pancreas cancers which consist of different pathologies.

WO 2004/091634 describes methods and compositions for augmenting treatment of different types of cancers and other proliferative disorders by combining the administration of an agent that inhibits the anti-apoptotic activity of galectin-3 (e.g., a "galectin-3 inhibitor") so as to potentiate the toxicity of a chemotherapeutic agent. However, galectin-3 does not play a role in the development of glioma (Camby et al., 2001a). The level of expression of galectin-3 dramatically decreases during the progression of the glioma disease and when tumor malignancy develops (Camby et al., 2001a). Therefore the use of an anti-galectin 3 strategy for therapeutic purpose to combat cancer in general cannot be extrapolated to glioma in particular. The above-described approaches, which are based on the anti-apoptotic activity of galectin-3, and the inhibition thereof, are therefore not effective in the treatment of glioma.

In view of the above, it is clear that there remains a need in the art for therapeutic approaches to combat cancer, in particular malignant gliomas, pancreatic cancer, head and neck cancer, melanoma, non-small-cell lung cancer and non-Hodgkin's lymphoma. It is therefore an object of the present invention to provide nucleic acid compounds, compositions and methods for the treatment of cancers, in particular cancers associated with galectin-1 expression or overexpression, and in particular, for the treatment of malignant glioma, pancreatic cancer, head and neck cancer, melanoma, non-small-cell lung cancer and non-Hodgkin's lymphoma, which overcome at least some of the drawbacks of currently applied compositions and methods.

SUMMARY

The present invention relates in general to a role of galectin-1 in the progression of malignancy in six cancer types and the present invention therefore relates to the use of an anti-galectin-1 therapeutic approach to combat human cancers in general, and malignant gliomas, pancreatic cancer, head and neck cancer, melanoma, non-small-cell lung cancer and non-Hodgkin's lymphoma in particular. The present therapeutic approach is in particular based on the use of anti-galectin-1 tools relating to RNA interference-(RNAi), antisense-, viral-vector-, or any other related approaches aiming to knock-down galectin-1 expression in human tumor astrocytes.

In a first aspect, the invention relates to the use of an RNA nucleic acid sequence to prepare an RNAi molecule suitable for reducing the expression of galectin-1 in tumor cells. More in particular, the invention relates to the use of an RNA sequence containing any of the sequences of SEQ ID NOs: 1 to 33, and preferably the sequences of SEQ ID NO: 2, 3 or 4, a fragment or derivative thereof, to prepare an RNAi molecule suitable for reducing the expression of galectin-1 in tumor cells.

The inventors surprisingly observed that the magnitude and duration of the downregulation of galectin-1 expression obtained with RNAi-related approach, in particular using siRNA, is by far larger than can be obtained using antisense oligonucleotide approaches. In addition, the RNAi approach is far more suitable for clinical application than an anti-sense oligonucleotide approach.

In addition, the inventors have surprisingly realized that RNAi molecules, e.g., siRNA, containing the sequence of SEQ ID NO: 2, a fragment or derivative thereof, display unexpectedly dramatic efficacy in reducing galectin-1 expression in tumor cells from gliomas, non-small-cell-lung cancers, pancreas cancers, head & neck cancers, non-Hodgkin's lymphomas and melanomas. The advantageous effectiveness of these RNAi molecules in down-regulating galectin-1, such as demonstrated in the examples and FIGS. 5 and 6 for "siRNA-1" (which contains the sequence of SEQ ID NO: 2) are highly surprising. Further advantage of RNAi molecules, e.g., siRNA, containing the sequence of SEQ ID NO: 2, a fragment or derivative thereof, is their high propensity to penetrate into tumor cells, and particularly in tumor cells from gliomas, non-small-cell-lung cancers, pancreas cancers, head & neck cancers, non-Hodgkin's lymphomas and melanomas (as observed in vitro by means of confocal microscopy and in vivo by means of fluorescence microscopy with fluorescent targeted SEQ ID NO:2 siRNA against gal-1).

In a second aspect, the invention relates to the use of a DNA nucleic acid sequence to prepare an RNAi molecule suitable for reducing the expression of galectin-1 in tumor cells. More in particular, the invention relates to the use of a DNA sequence, containing any of the sequences of SEQ ID NOs: 34 to 66, and preferably the sequences of SEQ ID NO: 35, 36, or 37, a fragment or derivative thereof, to prepare an RNAi molecule suitable for reducing the expression of galectin-1 in tumor cells. In a preferred embodiment, said DNA sequence is inserted in an expression vector suitable for the production of dsRNA. In another embodiment the invention also relates to an expression vector containing any of the sequences of SEQ ID NOs: 34 to 66, and preferably the sequences of SEQ ID NO: 35, 36, or 37, a fragment or derivative thereof.

In another aspect, the invention concerns the use of an RNAi molecule or an expression vector as defined herein as a medicament for treating glioma, pancreatic cancer, head and neck cancer, melanoma, non-small-cell lung cancer or non-Hodgkin's lymphoma, and/or for the manufacture of a medicament for treating glioma, pancreatic cancer, head and neck cancer, melanoma, non-small-cell lung cancer or non-Hodgkin's lymphoma.

In yet another aspect, the invention relates to a pharmaceutical composition for the treatment of glioma, pancreatic cancer, head and neck cancer, melanoma, non-small-cell lung cancer or non-Hodgkin's lymphoma, and/or for delaying the progression of glioma, pancreatic cancer, head and neck cancer, melanoma, non-small-cell lung cancer or non-Hodgkin's lymphoma, comprising an RNAi molecule or an expression vector as defined herein, and a pharmaceutically acceptable carrier.

In a further aspect, the invention also comprises a kit comprising a pharmaceutical composition as defined herein and an active compound for simulatenous, separate or sequential administration to a subject.

In other aspects the invention further relates to a method for treating glioma, pancreatic cancer, head and neck cancer, melanoma, non-small-cell lung cancer or non-Hodgkin's lymphoma, and to a method for delaying the progression of glioma, pancreatic cancer, head and neck cancer, melanoma, non-small-cell lung cancer or non-Hodgkin's lymphoma.

The present invention also provides a method for down-regulating galectin-1 expression in a tumor cell.

The present invention further relates to a method for reducing the migration of tumor cells, preferably cells of glioma, pancreatic cancer, head and neck cancer, melanoma, non-small-cell lung cancer or non-Hodgkin's lymphoma.

In yet another aspect, the invention further provides a method for reducing the resistance of tumor cells, preferably cells of glioma, pancreatic cancer, head and neck cancer, melanoma, non-small-cell lung cancer or non-Hodgkin's lymphoma to apoptosis, and a method for enhancing the efficacy of cancer therapies for the treatment of glioma, pancreatic cancer, head and neck cancer, melanoma, non-small-cell lung cancer or non-Hodgkin's lymphoma, selected from the group comprising chemotherapy, radiation therapy, immunotherapy, and/or gene therapy.

The present invention provides nucleic acids, RNAi molecules, compositions and methods for the treatment of glioma, pancreatic cancer, head and neck cancer, melanoma, non-small-cell lung cancer or non-Hodgkin's lymphoma, which have an activity which is different from a pro-apoptotic activity and which are based on down-regulation of galectin-1 expression in a respective tumor cell. The present invention provides nucleic acids, RNAi molecules, compositions and methods which are able to delay the progression of glioma cancer, pancreatic cancer, head and neck cancer, melanoma, non-small-cell lung cancer or non-Hodgkin's lymphoma, in affected subjects, and thus to increase the survival periods of patients. The present invention further provides new nucleic acids, RNAi molecules, compositions and methods that are able to decrease the levels of migration of tumor cells, preferably cells of glioma, pancreatic cancer, head and neck cancer, melanoma, non-small-cell lung cancer or non-Hodgkin's lymphoma. These agents may also restore a certain level of apoptosis in these migrating tumor cells, thereby restoring a certain level of sensitivity of these restricted-migratory tumor cells to current pro-apoptotic chemotherapeutic agents, and enhance the efficacy of pro-apoptotic cancer therapies. For example, such nucleic acids, RNAi molecules, compositions and methods are able to decrease the levels of migration of tumor astrocytes into the brain parenchyma, while restoring a certain level of apoptosis in these migrating tumor astrocytes. The present compositions and methods thus restore a certain level of sensitivity of these restricted-migratory tumor astrocytes to current pro-apoptotic chemotherapeutic agents, and enhance the efficacy of pro-apoptotic cancer therapies.

Additional aspects of the present invention will be apparent in view of the detailed description, which follows.

DESCRIPTION OF THE FIGURES

FIG. 1 represents the nucleic acid sequence of a *Homo sapiens* lectin, galactoside-binding, soluble, 1 (galectin 1), accession number BC020675, 556 bp FIG. 2 represents the nucleic acid sequence of a *Homo sapiens* lectin, galactoside-binding, soluble, 1 (galectin 1), accession number BC001693, 543 bp FIG. 3 represents the nucleic acid sequence of a *Homo sapiens* lectin, galactoside-binding, soluble, 1 (galectin 1), accession number NM_002305, 526 bp; with indication of the location of three putative siRNA sequences (SEQ ID NOs: 71 (underline), 72 (bold) and 73 (bold and underlined))

FIG. 4 represents the secondary structure of two siRNA molecules.

DETAILED DESCRIPTION OF THE INVENTION

Introduction

Figure 5A:
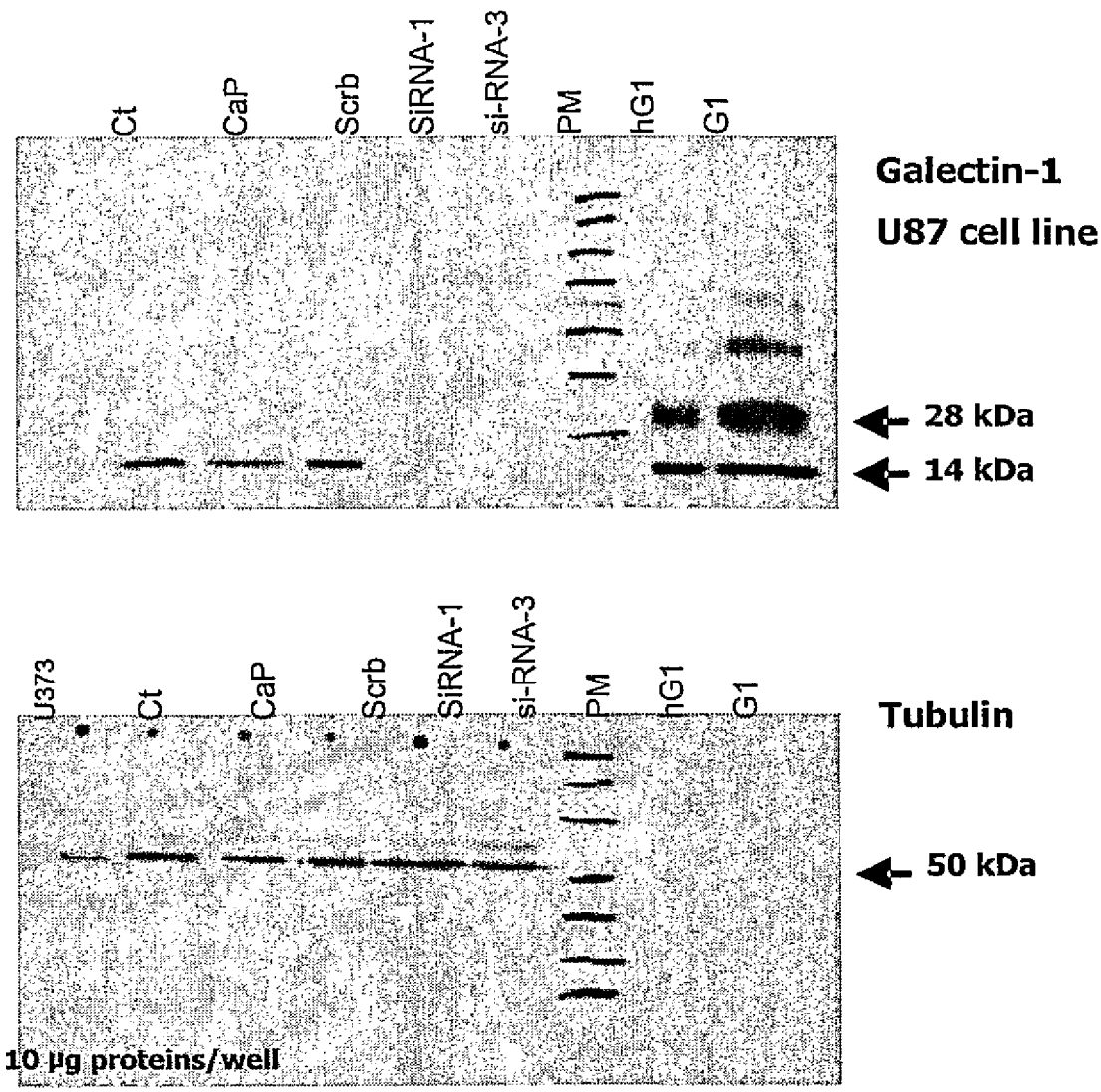
FIG. 5 illustrates protein expression by means of a Western blot (FIG. 5A) and immunocytochemical fluorescent stainings (FIG. 5B) of galectin-1 in cells transfected with a siRNA molecule according to the invention.

Gliomas account for more than 50% of all brain tumors and are by far the most common primary brain tumors in children and in adults (Kleihues and Cavenee 2000; Lefranc et al., 2005a). They include three histopathological subgroups characterized by different levels of aggressiveness and malignancy, i.e. ependymomas (<10% of all gliomas), oligodendrogliomas (5-30% of all gliomas) and astrocytomas (60-70% of all gliomas). Malignant astrocytic gliomas are associated with the worst prognoses because of their ability to infiltrate diffusely into the normal brain parenchyma and therefore include World Health Organization (WHO) grades II, III and grade IV tumors (Kleihues and Cavenee 2000; Lefranc et al., 2005a). In the case of patients suffering from these tumors, the prognosis remains dismal (Kleihues and Cavenee 2000). The median survival period for patients with glioblastomas (WHO grade IV), the most malignant form of all glial tumor types, is in the range of 1 year, even with aggressive multimodal treatment. To date, no single glioblastoma patient has been cured (Lefranc et al., 2005a). Glioblastoma accounts for about 50% of all glial tumors, i.e. 2 to 3% of all solid tumors in adults and up to 10-15% of all solid tumors in children. Malignant gliomas are thus among the most challenging of all cancers to treat successfully because they are characterized not only by aggressive proliferation and expansion, but also by their inexorable invasion of distant brain tissue (Lefranc et al., 2005a).

The high level of tumor astrocytes in the brain parenchyma leads to the rapid recurrence of glial tumors (within 3-6 months) predominantly adjacent to resection cavities, but also at distance from the primary sites. The levels of tumor astrocyte migration into the brain parenchyma cannot be decreased by radiotherapy and/or chemotherapy because i) migrating tumor astrocytes are resistant to apoptosis, and ii) radiotherapy and most of the chemotherapeutic agents used today are pro-apoptotic agents (Lefranc et al., 2005a).

In view hereof it is clear that there is a great need in the prior art for new types of therapeutic approaches that are independent of the apoptotic pathway(s) to combat malignant gliomas.

A number of signaling pathways is activated in migrating glioma cells. It has been suggested to treat malignant glioma, by using inhibitors against one or more signaling pathways involved in cell migration. However, a major disadvantage is that these pathways are not all constitutively activated at the same time in any one glioma (Lefranc et al., 2005a). In order to be successful such strategy would therefore require the application of particular inhibitors only if the corresponding target is present in the tumor tissue. Such strategies would thus require individual patients to be submitted to a molecular profiling of their tumors before undergoing any treatment to combat their migratory glioma cells. It is clear that such strategies are far from efficient, cost-effective, and would involve a precious delay of time before effective treatment could be started (Lefranc et al., 2005a).

Pancreatic cancer or pancreatic carcinoma most commonly refers to ductal adenocarcinomas. These are exocrine or ductal pancreatic cancers, which constitute more than 90% of the diagnosed cases of pancreatic cancer. Islet cell tumors or tumors of the endocrine pancreas typically constitute less than 10% of the diagnosed cases.

Head and neck cancer encompasses any carcinoma in tissues of the head and neck region of a subject. Such head and neck carcinomas include, for example, carcinoma of the mouth, esophagus, throat, larynx, thyroid gland, tongue, lips, salivary glands, nose, paranasal sinuses, nasopharynx, superior nasal vault and sinus tumors, esthesioneuroblastoma, squamous cell cancer, malignant melanoma, sinonasal undifferentiated carcinoma (SNUC) or blood neoplasia. Also included are carcinoma's of the regional lymph nodes including cervical lymph nodes, prelaryngeal lymph nodes, pulmonary juxtaesophageal lymph nodes and submandibular lymph nodes (Harrison's Principles of Internal Medicine, eds., Isselbacher, et al., McGraw-Hill, Inc., 13th Edition, pp 1850-1853, 1994).

Melanoma refers to a malignant or benign tumor arising from the melanocytic system of the skin and other organs, including, e.g., the oral cavity, esophagus, anal canal, vagina, leptomeninges and/or the conjunctivae or eye. Non-limiting examples of melanoma include acral-lentiginous melanoma, amelanotic melanoma, benign juvenile melanoma, lentigo maligna melanoma, malign melanoma, nodular melanoma, subungual melanoma, superficial spreading melanoma, etc.

Non-small-cell lung cancer (NSCLC) includes any of the three subtypes thereof, i.e., adenocarcinoma of the lung, squamous cell carcinoma of the lung and large cell carcinoma of the lung.

Lymphomas are cancers that develop in lymphocytes. They are broadly classified into two categories—Hodgkin's disease and non-Hodgkin's lymphoma. The term "non-Hodgkin's lymphoma" is broad and encompasses all the lymphomas that are not Hodgkin's disease. Lymphomas are divided into three types depending on how quickly and aggressively they grow: low-grade are the slowest growing types and sometimes are called "indolent" lymphomas; intermediate-grade lymphomas grow quickly; and high-grade lymphomas are the fastest and most aggressively growing types.

However, so far, no suitable strategies have been developed based on galectin-1 as target for combating human cancer, including the above pancreatic cancer, head and neck cancer, melanoma, NSCLC, non-Hodgkin's lymphoma and glioma. The applicant now presents an improved strategy to combat human cancers in general, and malignant human gliomas and preferably glioblastoma, pancreatic cancer, head and neck cancer, melanoma, non-small-cell lung cancer and non-Hodgkin's lymphoma in particular which is based on an anti-galectin-1 therapeutic approach. The present invention has several aspects, related with the role of galectin-1 in the development and malignancy of cancer, and in particular of glioma, pancreatic cancer, head and neck cancer, melanoma, non-small-cell lung cancer and non-Hodgkin's lymphoma. More in particular, the invention relates to the use of RNA interference (RNAi) to effect knockdown of expression of a target gene, and in particular of the galectin-1 gene.

Definitions

The term "apoptosis" as used herein refers to the physiological process by which unwanted or useless cells are eliminated during development and other normal biological processes. Apoptosis is a mode of cell death that occurs under normal physiological conditions and the cell is an active participant in its own demise ("cellular suicide").

A "target gene" as used herein means a gene that needs to be silenced in a subject, and in particular refers herein to the human galectin-1 gene.

"RNA interference" or "RNAi" is a term initially applied to a phenomenon observed in plants and worms where double-stranded RNA (dsRNA) blocks gene expression in a specific and post-transcriptional manner. RNAi provides a useful method of inhibiting gene expression in vitro or in vivo.

In the present context, the expression "dsRNA" relates to double stranded RNA capable of causing RNA interference. In accordance with the present invention, any suitable double-stranded RNA fragment capable of directing RNAi or RNA-mediated gene silencing of a target gene can be used. As used herein, a "double-stranded ribonucleic acid molecule (dsRNA)" refers to any RNA molecule, fragment or segment containing two strands forming an RNA duplex, notwithstanding the presence of single stranded overhangs of unpaired nucleotides. The double-stranded RNA comprises annealed complementary strands, one of which has a nucleotide sequence which corresponds to a target nucleotide sequence (i.e. to at least a portion of the mRNA transcript) of the target gene to be down-regulated. The other strand of the double-stranded RNA is complementary to this target nucleotide sequence.

The double-stranded RNA need only be sufficiently similar to the mRNA sequence of the target gene to be down-regulated that it has the ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and a nucleotide sequence of the dsRNA sequence is no more than 1 in 5 basepairs, or 1 in 10 basepairs, or 1 in 20 basepairs, or 1 in 50 basepairs.

According to the invention, the "dsRNA" or "double stranded RNA", whenever said expression relates to RNA that is capable of causing interference, may be formed form two separate (sense and antisense) RNA strands that are annealed together. Alternatively, the dsRNA may have a foldback stem-loop or hairpin structure wherein the two annealed strands of the dsRNA are covalently linked. In this embodiment, the sense and antisense strands of the dsRNA are formed from different regions of a single RNA sequence that is partially self-complementary.

As used herein, the term "RNAi molecule" is a generic term referring to double stranded RNA molecules including small interfering RNAs (siRNAs), hairpin RNAs (shRNAs), and other RNA molecules which can be cleaved in vivo to form siRNAs. RNAi molecules can comprise either long stretches of dsRNA identical or substantially identical to the target nucleic acid sequence or short stretches of dsRNA identical or substantially identical to only a region of the target nucleic acid sequence.

The subject RNAi molecules can be "small interfering RNAs" or "siRNAs." siRNA molecules are usually synthesized as double stranded molecules in which each strand is around 19-30 nucleotides in length, and even more preferably 21-23 nucleotides in length. The siRNAs are understood to recruit nuclease complexes and guide the complexes to the target mRNA by pairing to the specific sequences. As a result, the target mRNA is degraded by the nucleases in the protein complex. In a particular embodiment, the siRNA molecules comprise a 3' hydroxyl group. In certain embodiments, the siRNA constructs can be generated by processing of longer double-stranded RNAs, for example, in the presence of the enzyme dicer.

Alternatively, the RNAi molecule is in the form of a hairpin structure, named as hairpin RNA or shRNA. The hairpin RNAs can be synthesized exogenously or can be formed by transcribing from RNA polymerase III promoters in vivo. Preferably, such hairpin RNAs are engineered in cells or in an animal to ensure continuous and stable suppression of a desired gene. It is known in the art that siRNAs can be produced by processing a hairpin RNA in the cell.

The present RNAi molecules may include modifications to either the phosphate-sugar backbone or the nucleoside, e.g., to reduce susceptibility to cellular nucleases, improve bioavailability, improve formulation characteristics, and/or change other pharmacokinetic properties.

In some cases, at least one strand of the RNAi molecules has a 3' overhang from about 1 to about 6 nucleotides in length, and for instance from 2 to 4 nucleotides in length. More preferably, the 3' overhangs are 1-3 nucleotides in length. In certain embodiments, one strand has a 3' overhang and the other strand is blunt-ended or also has an overhang. The length of the overhangs may be the same or different for each strand. In order to further enhance the stability of the RNAi molecules, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythymidine is tolerated and does not affect the efficiency of RNAi.

Production of RNAi molecules can be carried out by chemical synthetic methods or by recombinant nucleic acid techniques. The RNAi molecules may be produced enzymatically or by partial/total organic synthesis. Any modified ribonucleotide can be introduced by in vitro enzymatic or organic synthesis.

The RNAi molecules can be purified using a number of techniques known to those of skill in the art. For example, gel electrophoresis can be used to purify RNAi molecules. Alternatively, non-denaturing methods, such as non-denaturing column chromatography, can be used to purify the RNAi molecules. In addition, chromatography (e.g., size exclusion chromatography), glycerol gradient centrifugation, affinity purification with antibody can be used to purify RNAi molecules.

Nucleic Acids, RNAi Molecules and Expression Constructs

The invention is in one aspect related to the use of a nucleic acid sequence, to prepare an RNAi molecule suitable for reducing the expression of a target gene, preferably the galectin-1 in tumor cells.

As used herein the term "reducing the expression of a target gene" refers to the ability of the present RNAi molecules to block expression of the target gene in a specific and post-transcriptional manner.

In a preferred embodiment the invention relates to the use of an RNA sequence to prepare an RNAi molecule as defined herein, and preferably a siRNA molecule. Said siRNA molecule is characterized by one or more, and preferably by all of the following criteria:
- having at least 50% sequence identity, preferably at least 70% sequence identity, more preferred at least 80% sequence identity, even more preferred at least 90% sequence identity with the target mRNA;
- having a sequence which targets the exon area of the target gene;
- showing a preference for targeting the 3' end of the target gene rather than for targeting the 5' end of the target gene.

In a further preferred embodiment, the siRNA molecule may be further characterized by one or more of the following criteria:
- having a nucleic acid length of between 15 to 25 nucleotides and preferably of between 18 to 22 nucleotides, and preferably of 19 nucleotides;
- having a GC content comprised between 30 and 50%
- showing a TT(T) sequence at its 3' end;
- showing no secondary structure when adopting the duplex form;
- having a Tm (melting temperature) of lower than 20° C.
- having the nucleotides indicated in Table I in the sequence of the nucleotides, wherein h is a, c, t/u but not g, and wherein d is a, g, t/u but not c, and wherein w is a or t/u, but not g or c:

TABLE I

|  |  | — | — | 1 | 2 | 3 | 4 | 5 | 6 | 7 | 8 | 9 | 10 | 11 | 12 | 13 | 14 | 15 | 16 | 17 | 18 | 19 | — | — |
|---|---|---|---|---|---|---|---|---|---|---|---|---|---|---|---|---|---|---|---|---|---|---|---|---|
| mRNA | P'5 |  |  | A | A |  | A |  |  |  |  |  | U |  | h |  |  |  | w |  |  |  | 3'-OH |  |
| si-ASense | OH-3' | T | T |  |  | U |  |  |  |  |  |  | A |  | d |  |  |  | w |  |  |  | 5'-P |  |
| si-Sense | P-5' |  |  |  | A |  |  |  |  |  |  |  | U |  | h |  |  |  | w | T | T |  | 3'-OH |  |

In a preferred embodiment, the invention is related to the use of an RNA sequence containing any of the sequences of:

```
5'-aucagccagcccauggccc-3'       (SEQ ID NO: 1)
5'-gcugccagauggauacgaa-3',      (SEQ ID NO: 2)
5'-agacagcaacaaccugugc-3'       (SEQ ID NO: 3)
5'-guguugcagaggugugcau-3'       (SEQ ID NO: 4)
5'-cauccuccuggacucaauc-3'       (SEQ ID NO: 5)
5'-ucauggcuugugucuggu-3'        (SEQ ID NO: 6)
5'-ccugaaucucaaaccugga-3'       (SEQ ID NO: 7)
5'-ucucaaaccuggagugc-3'         (SEQ ID NO: 8)
5'-accuggagagugccuucga-3'       (SEQ ID NO: 9)
5'-ccuggagagugccuucgag-3'       (SEQ ID NO: 10)
5'-gagcuucgugcugaaccug-3'       (SEQ ID NO: 11)
5'-ccugggcaaagacagcaac-3'       (SEQ ID NO: 12)
5'-gacagcaacaaccugugcc-3'       (SEQ ID NO: 13)
5'-caaccugugccugcacuuc-3'       (SEQ ID NO: 14)
5'-ccugugccugcacuucaac-3'       (SEQ ID NO: 15)
5'-cccucgcuucaacgcccac-3'       (SEQ ID NO: 16)
5'-cgcccacggcgacgccaac-3'       (SEQ ID NO: 17)
5'-caccaucgugugcaacagc-3'       (SEQ ID NO: 18)
5'-cagcaaggacggcggggcc-3'       (SEQ ID NO: 19)
5'-ggacggcggggccuggggg-3'       (SEQ ID NO: 20)
5'-ccugaccgucaagcugcca-3'       (SEQ ID NO: 21)
5'-uucaaguuccccaaccgcc-3'       (SEQ ID NO: 22)
5'-guuccccaaccgccucaac-3'       (SEQ ID NO: 23)
5'-ccgccucaaccuggaggcc-3'       (SEQ ID NO: 24)
5'-ccuggaggccaucaacuac-3'       (SEQ ID NO: 25)
5'-cuacauggcagcugacggu-3'       (SEQ ID NO: 26)
5'-gaucaaaugugugugccuuu-3'      (SEQ ID NO: 27)
5'-auguguggccuuugacuga-3'       (SEQ ID NO: 28)
5'-uguguggccuuugacugaa-3'       (SEQ ID NO: 29)
5'-ucagccagcccauggcccc-3'       (SEQ ID NO: 30)
5'-uaaaggcagcugccucugc-3'       (SEQ ID NO: 31)
5'-aggcagcugccucugcucc-3',      (SEQ ID NO: 32)
5'-ggcagcugccucugcuccc-3',      (SEQ ID NO: 33)
``` a fragment or derivative thereof, to prepare an RNAi molecule suitable for reducing the expression of galectin-1 in tumor cells.

In the context of the present invention, the terms "fragment and derivative" refer to nucleic acids that may differ from the original nucleic acid in that they are extended or shortened on either the 5' or the 3' end, on both ends or internally, or extended on one end, and shortened on the other end, provided that the function of the resulting RNAi molecule, namely the down-regulation of the target gene, is not abolished or inhibited. The term "fragment and derivative" also refers to nucleic acids that may differ from the original nucleic acid in that one or more nucleotides of the original sequence are substituted by other nucleotides and/or (chemically) modified by methods available to the skilled person, provided that the function of the resulting RNAi molecule is not abolished or inhibited. The "fragment and derivative" may typically show at least 80%, e.g., at least 85%, preferably at least 90%, e.g., at least 95% or even at least 99% sequence identity to the original nucleic acid. Sequence identity between two nucleotide sequences can be calculated by aligning the said sequences and determining the number of positions in the alignment at which the two sequences contain the same nucleic acid base vs. the total number of positions in the alignment.

It shall be clear to a person of skilled in the art that any of the above-given sequences or complementary sequences thereof may be used to prepare an RNAi molecule, i.e. a double stranded RNA molecule. The person of skill in the art knows how to prepare an RNAi molecule when the above disclosed nucleic acids, particularly RNAs, are provided. Briefly, the strands complementary to the nucleic acids of the present invention are synthesized by any available method and the complementary strands are annealed to the nucleic acid of the present invention under appropriate conditions. The annealing conditions, e.g. temperatures and incubation periods, may be adjusted according to the respective nucleic acid sequence.

In a preferred embodiment the invention relates to the use of an RNA sequence containing the sequence of SEQ ID NO:2, a fragment or derivative thereof, to prepare an RNAi molecule, and preferably an siRNA molecule. Preferably, the double stranded siRNA molecule which is obtained using the sequence with SEQ ID NO:2 is herein also indicated with siRNA-1.

In another preferred embodiment the invention relates to the use of an RNA sequence containing the sequence of SEQ ID NO:3, a fragment or derivative thereof, to prepare an RNAi molecule, and preferably an siRNA molecule. Preferably, the double stranded siRNA molecule which is obtained using the sequence with SEQ ID NO:3 is herein also indicated with siRNA-2.

In a yet another preferred embodiment, the invention relates to the use of an RNA sequence containing the sequence of SEQ ID NO:4, a fragment or derivative thereof, to prepare an RNAi molecule, and preferably an siRNA molecule. Preferably, the double stranded siRNA molecule which is obtained using the sequence with SEQ ID NO:4 is herein also indicated with siRNA-3.

In order to exert the desired function, i.e. reducing the expression of galectin-1 in tumor cells, the RNAi molecules according to the invention, and in particular the siRNA molecules, prepared from ribonucleic acids of the present invention as defined above, are delivered into target cells, preferably human cancer cells, e.g., human glial cells or cells of pancreatic cancer, head and neck cancer, melanoma, non-small-cell lung cancer or non-Hodgkin's lymphoma.

There are several well-known methods of introducing (ribo)nucleic acids into animal cells, any of which may be used in the present invention and which depend on the host. At the simplest, the nucleic acid can be directly injected into the target cell/target tissue. Other methods include fusion of the recipient cell with bacterial protoplasts containing the nucleic acid, the use of compositions like calcium chloride, rubidium chloride, lithium chloride, calcium phosphate, DEAE dextran, cationic lipids or liposomes or methods like receptor-mediated endocytosis, biolistic particle bombardment ("gene gun" method), infection with viral vectors, electroporation, and the like. Other techniques or methods which are suitable for delivering RNAi molecules as defined herein to target cells include the continuous delivery of an RNAi molecule as defined herein from poly(lactic-Co-Glycolic Acid) polymeric microspheres (see Benny et al. 2005) or the direct injection of protected (stabilized) RNAi molecule(s) into micropumps delivering the product in the hole of surgical resection to the tumor cells still present at the site of surgery, e.g., in the hole of neurosurgical resection to the tumor cells still present in the brain parenchyma, as was detailed previously for the use of other anti-migratory compounds (see Lefranc et al. 2003). Convection-enhanced delivery, as detailed by Kawakami et al. (2004) of stabilized RNAi molecules as defined herein can also be used. Another possibility is the use of implantable drug-releasing biodegradable micropsheres, as those recently reviewed by Menei and Benoit (2003). It shall be clear that also a combination of different above-mentioned delivery modes or methods may be used.

A preferred approach is to use either an Ommaya reservoir (micropumps) delivering the present RNAi molecule(s) versus encapsulated RNAi molecules in biodegradable microspheres, or both approaches at the same time. A similar approach based on the use of micropumps can be employed for the five other types of cancer (in addition to gliomas) under the interest of the present invention, i.e. non-Hodgkin's lymphomas, pancreas cancers, head & neck cancers, melanomas and non-small-cell-lung cancers (NSCLC).

The main obstacle to achieve in vivo gene silencing by RNAi technologies is delivery. To improve thermal stability, resistance to nuclease digestion and to enhance cellular uptake of the RNAi tools, various approaches were tested. They include:

chemical modifications like locked nucleic acid (LNA, Elmen et al. 2005), phosphorothioate substitution (Harboth et al. 2003), 2'-fluoro substitution (Harboth et al. 2003), 2'-O-methyl substitution (Czauderna et al. 2003), stabilized stealth™ RNAi (Invitrogen), etc.

encapsulation of RNAi tools in various types of liposomes (immunoliposomes, PEGylated (immuno) liposomes), cationic lipids and polymers, nanoparticules or dendrimers, poly(lactic-Co-Glycolic Acid) polymeric microspheres, implantable drug-releasing biodegradable microspheres, etc (Zhang et al. 2004, Shi et al. 2000; Schiffelers et al. 2004).

co-injection of the RNAi tools with protective agent like the nuclease inhibitor aurintricarboxylic acid (Spankuch et al. 2004).

Preferably, the RNAi tools of the present invention, optionally stabilized, encapsulated or otherwise modified as above, may be delivered at the site of the tumor, e.g., the primary tumor and/or metastases. A manner of achieving localized delivery is the use of the Ommaya reservoir as described elsewhere. Another way of targeting the present RNAi tools to tumor cells is to use antibody-directed, cell type-specific delivery.

For example, RNAi (e.g., siRNA) can be complexed with Fab specifically recognizing tumor cells, such as Fab-protamine-complexed (Song et al., 2005), or RNAi may be encapsulated in immunoliposomes. Such antibody-targeted RNAi tools, e.g., in the form of nanoparticles, can be administrated by various means, such as systemic administration (i.v. injection, subcutaneous injection, intramuscular injection, oral administration, nasal inhalation, etc.) or locally, e.g., using an Ommaya reservoir. Antibody-targeted delivery may prove particularly useful for treatment of tumors developing in tissues that naturally express galectin-1. In this case, the immuno-targeting of tumor cells would minimize side effects relating to downregulation of galectin-1 expression in the normal tissue surrounding the tumor.

Inhalative administration of the present RNAi tools, e.g., in the form of nasal sprays or aerosol mixtures, may be employed, and may be particularly useful for head and neck cancers, e.g., some types of head and neck squamous cell carcinomas, and for non-small cell lung cancers.

In vivo delivery of siRNA has been described, e.g., intravenous (Schiffelers et al., 2004; Morrissey et al., 2005), intracerebroventricular (Thakker et al., 2004) or intranasal (Zhang et al., 2005) administration of naked or lipid-encapsulated siRNA molecules; intravenous administration of shRNA vectors encapsulated in immunoliposomes or in viral particles are also described (Spankuch et al., 2004; Zhang et al., 2004); herein incorporated by reference.

The effect of the RNAi molecule, i.e. the reduction of the expression of a target gene, is considered to be only transient when the molecules are directly applied to cells as for instance described supra. In order to achieve a stable production of RNAi molecules in tumor cells it can be advantageous if a nucleic acid, preferably a DNA, encoding the respective target RNAi molecule is integrated in an expression vector. Providing suitable elements, as described hereinafter, the DNA is transcribed into the corresponding double stranded RNA which is capable of forming the desired RNAi molecule.

Thus, according to a further aspect of the present invention, expression constructs are provided to facilitate introduction into a host cell and/or facilitate expression and/or facilitate maintenance of the nucleotide sequence encoding the RNAi molecules according to the invention. The expression constructs may be inserted into a plasmid, a virus, or a vector, which may be commercially available.

In another embodiment, the invention therefore relates to the use of a DNA sequence to prepare an RNAi molecule as defined herein, and preferably a siRNA molecule. More in particular, the invention relates to the use of a DNA sequence containing any of the sequences of SEQ ID NOs:34-66,

```
                                              (SEQ ID NO: 34)
5'-atcagccagcccatggccc(N)xgggccatgggctggctgat-3'

(SEQ ID NO: 35)
5'-gctgccagatggatacgaa(N)xttcgtatccatctggcagctt-3', (SEQ ID NO: 36)
5'-agacagcaacaacctgtgc(N)xgcacaggttgttgctgtcttt-3'

(SEQ ID NO: 37)
5'-gtgttgcagaggtgtgcat(N)xatgcacacctctgcaacactt-3'

(SEQ ID NO: 38)
5'-catcctcctggactcaatc(N)xgattgagtccaggaggatgtt-3'

(SEQ ID NO: 39)
5'-tcatggcttgtggtctggt(N)xaccagaccacaagccatgatt-3'

(SEQ ID NO: 40)
5'-cctgaatctcaaacctgga(N)xtccaggtttgagattcaggtt-3'

(SEQ ID NO: 41)
5'-tctcaaacctggagagtgc(N)xgcactctccaggtttgagatt-3'

(SEQ ID NO: 42)
5'-acctggagagtgccttcga(N)xtcgaaggcactctccaggttt-3'

(SEQ ID NO: 43)
5'-cctggagagtgccttcgag(N)xctcgaaggcactctccaggtt-3'

(SEQ ID NO: 44)
5'-gagcttcgtgctgaacctg(N)xcaggttcagcacgaagctctt-3'

(SEQ ID NO: 45)
5'-cctgggcaaagacagcaac(N)xgttgctgtctttgcccaggtt-3'

(SEQ ID NO: 46)
5'-gacagcaacaacctgtgcc(N)xggcacaggttgttgctgtctt-3'

(SEQ ID NO: 47)
5'-caacctgtgcctgcacttc(N)xgaagtgcaggcacaggttgtt-3'

(SEQ ID NO: 48)
5'-cctgtgcctgcacttcaac(N)xgttgaagtgcaggcacaggtt-3'

(SEQ ID NO: 49)
5'-ccctcgcttcaacgcccac(N)xgtgggcgttgaagcgaggtt-3'

(SEQ ID NO: 50)
5'-cgcccacggcgacgccaac(N)xgttggcgtcgccgtgggcgtt-3'

(SEQ ID NO: 51)
5'-caccatcgtgtgcaacagc(N)xgctgttgcacacgatggtgtt-3'

(SEQ ID NO: 52)
5'-cagcaaggacggcggggcc(N)xggccccgccgtccttgctgtt-3'

(SEQ ID NO: 53)
5'-ggacggcggggcctggggg(N)xcccccaggccccgccgtcctt-3'

(SEQ ID NO: 54)
5'-cctgaccgtcaagctgcca(N)xtggcagcttgacggtcaggtt-3'

(SEQ ID NO: 55)
5'-ttcaagttccccaaccgcc(N)xggcggttggggaacttgaatt-3'

(SEQ ID NO: 56)
5'-gttccccaaccgcctcaac(N)xgttgaggcggttggggaactt-3'

(SEQ ID NO: 57)
5'-ccgcctcaacctggaggcc(N)xggcctccaggttgaggcggtt-3'

(SEQ ID NO: 58)
5'-cctggaggccatcaactac(N)xgtagttgatggcctccaggtt-3'

(SEQ ID NO: 59)
5'-ctacatggcagctgacggt(N)xaccgtcagctgccatgtagtt-3'

(SEQ ID NO: 60)
5'-gatcaaatgtgtggccttt(N)xaaaggccacacatttgatctt-3'

(SEQ ID NO: 61)
5'-atgtgtggcctttgactga(N)xtcagtcaaaggccacacattt-3'

(SEQ ID NO: 62)
5'-tgtgtggcctttgactgaa(N)xttcagtcaaaggccacacatt-3'

(SEQ ID NO: 63)
5'-tcagccagcccatggcccc(N)xggggccatgggctggctgatt-3'

(SEQ ID NO: 64)
5'-taaaggcagctgcctctgc(N)xgcagaggcagctgcctttatt-3'

(SEQ ID NO: 65)
5'-aggcagctgcctctgctcc(N)xggagcagaggcagctgcctt-3'

(SEQ ID NO: 66)
5'-ggcagctgcctctgctccc(N)xgggagcagaggcagctgcctt-3'
``` wherein N is a, c, t or g and wherein x is comprised between 4 and 15, a fragment or derivative thereof, to prepare a RNAi molecule suitable for reducing the expression of galectin-1 in tumor cells.

The above enumerated sequences with SEQ ID NOs: 34-66 comprise the DNA sequences which correspond to the RNA sequences respectively depicted in SEQ ID NOs:1-33, a linker, and the sequence complementary to said DNA. The linker is preferably 4 to 15 nucleotides in length, more preferably the linker is 4 to 10 nucleotides long and most preferably it is 4 to 8 nucleotides long. The linker can consist of any suitable nucleotide sequence. Preferably said enumerated sequences consists of 19 nt sequences derived form the galectin-1 gene which are separated by a 4 to 15 nucleotide linker (higher case letter N, wherein N is a, c, t or g and wherein x is comprised between 4 and 15), from the reverse complement of the same 19 nt sequences and showing an tt(t) sequence at its 3' end.

In another embodiment, the above enumerated DNA sequences are inserted into an expression vector, and preferably in an expression vector which allows for the production of dsRNA.

In yet another embodiment, the invention relates to an expression vector containing any of the sequences of SEQ ID NO: 34 to 66, and preferably the sequences of SEQ ID NO: 35, 36, or 37, a fragment or derivative thereof.

It is also contemplated in the present invention that the expression of the two complementary strands giving rise to a dsRNA is driven from two promoters, either the same or different. In this case, the nucleotide linker separating the two complementary strands would be omissible. It is further obvious to the one skilled in the art that in this case the DNAs coding for the two complementary siRNA strands can be present on one or on two expression vectors.

Expression vectors, capable of giving rise to transcripts which form dsRNA as defined herein, can for instance be cloning vectors, binary vectors or integrating vectors. The invention thus also relates to a vector comprising any of the DNA sequences as described above. The expression vector is preferably a eukaryotic expression vector, or a retroviral vector, a plasmid, bacteriophage, or any other vector typically used in the biotechnology field. Such vectors are known to the person skilled in the art. If necessary or desired, the DNA nucleic acid can be operatively linked to regulatory elements which direct the synthesis of mRNA in eukaryotic cells.

The terms "regulatory sequences" and "control sequence" used herein are to be taken in a broad context and refer to regulatory nucleic acid sequences capable of driving and/or regulating expression of the sequences to which they are ligated and/or operably linked. For expression in eukaryotes, control sequences generally include promoters, terminators and, in some instances, enhancers, and/or 5' and 3' untranslated sequences, but can also comprise introns or similar elements, for example those, which promote or contribute to the stability and the amplification of the vector, the selection for successful delivery and/or the integration into the host's genome, like regions that promote homologous recombination at a desired site in the genome. The term "control sequence" is intended to include, at a minimum, all components necessary for expression, and may also include additional advantageous components. The term "control sequence" encompasses a promoter or a sequence capable of activating or enhancing expression of a nucleic acid molecule in a cell, tissue or organ.

To drive the expression of dsRNA these vectors usually contain an RNA Pol I, an RNA Pol II, an RNA Pol III, T7 RNA polymerase or SP6 RNA polymerase and preferably RNA polymerase III promoters, such as the H1 or U6 promoter, since RNA polymerase III expresses relatively large amounts of small RNAs in mammalian cells and terminates transcription upon incorporating a string of 3-6 uridines. Type III promoters lie completely upstream of the sequence being transcribed which eliminates any need to include promoter sequence in the RNAi molecule. If the DNA encoding the desired RNAi molecule is to be transcribed from one promoter, the preferred DNA thus contains on each of its strands the desired coding region of the target gene and its reverse complementary sequence, wherein the coding and its reverse complementary sequences are separated by a nucleotide linker, allowing for the resulting transcript to fold back on itself to form a so-called stem-loop structure, and to form so-called shRNA molecules. The shRNA is transcribed from specific promoters, processed by the DICER RNAse into short double stranded RNA (siRNA) and incorporated into RISC (Dykxhoorn et al. 2003) with subsequent inactivation of the targeted mRNA.

Optionally, one or more transcription termination sequences may also be incorporated in the expression vector. The term "transcription termination sequence" encompasses a control sequence at the end of a transcriptional unit, which signals 3' processing and poly-adenylation of a primary transcript and termination of transcription. Additional regulatory elements, such as transcriptional or translational enhancers, may be incorporated in the expression construct.

For therapeutic purposes, the use of retroviral vectors has been proven to be most appropriate to deliver a desired nucleic acid into a target cell.

The RNAi expression vectors containing the DNA sequences of the present invention can be introduced into the target cell by any of the delivery method described above.

Uses, Compositions and Kits

The RNAi molecules and/or vectors according to the present invention may be used as a medicament for treating cancer, preferably glioma, pancreatic cancer, head and neck cancer, melanoma, non-small-cell lung cancer or non-Hodgkin's lymphoma, or for the manufacture of a medicament for treating cancer, preferably glioma (preferably for treating glioblastoma), pancreatic cancer, head and neck cancer, melanoma, non-small-cell lung cancer or non-Hodgkin's lymphoma.

The RNAi molecules and/or vectors according to the present invention may also be used as a medicament for delaying the progression of cancer, preferably glioma, pancreatic cancer, head and neck cancer, melanoma, non-small-cell lung cancer or non-Hodgkin's lymphoma, or for the manufacture of a medicament for delaying the progression of cancer, preferably glioma (preferably of glioblastoma), pancreatic cancer, head and neck cancer, melanoma, non-small-cell lung cancer or non-Hodgkin's lymphoma.

The term "delaying the progression of cancer" as used herein, refers to a delay in cancer re-growth by more than 30%, and preferably by more than 50% and even more preferred by more than 70% and/or to an increase the survival periods of affected subjects.

The RNAi molecules and/or vectors according to the present invention may be used alone or in combination with any of the cancer therapies selected from the group comprising chemotherapy, radiation therapy, immunotherapy, and/or gene therapy.

As used herein the term "cancer therapy" is meant to encompass radiation therapy, chemotherapy, immunotherapy, gene-based therapy as well as combinations thereof. The term "radiation therapy" refers to the treatment of cancer using radiation. The term "chemotherapy" refers to the treatment of cancer with chemical substances, so-called chemotherapeutics. The term "immunotherapy" as used herein refers to the stimulation of the reactivity of the immune system towards eliminating the cancer cells by using immunotherapeutics. The term "gene-based therapy" refers to the treatment of cancer based upon the transfer of genetic material (DNA, or possibly RNA) into an individual.

In another preferred embodiment the present RNAi molecules and/or expression vectors may be used alone or in combination with one or more active compounds that are suitable in the treatment of cancer, preferably glioma, pancreatic cancer, head and neck cancer, melanoma, non-small-cell lung cancer or non-Hodgkin's lymphoma. The term "active compound" refers to a compound other than RNAi molecules or vectors which is used to treat cancer, preferably glioma, pancreatic cancer, head and neck cancer, melanoma, non-small-cell lung cancer or non-Hodgkin's lymphoma. The active compounds may preferably be selected from the group comprising radiation therapeutics, chemotherapeutics including but not limited to temozolomide, vincristine, vinorelbine, procarbazine, carmustine, lomustine, taxol, taxotere, tamoxifen, retinoic acid, 5-fluorouracil, cyclophosphamide and thalidomide, immunotherapeutics such as but not limited to activated T cells and pulsed dendritic cells, and/or gene-based therapeutic approached involving gene transfer of CD3, CD7 and CD45 in glioma cells, concomitantly with the delivery of an RNAi molecule as defined herein.

The RNAi molecules and/or expression vectors of the present invention can be administered alone or in combination with one or more active compounds. The latter can be administered before, after or simultaneously with the administration of RNAi molecules and/or expression vectors. The dose of RNAi molecules and/or expression vectors according to the invention or the active compound as well as the duration and the temperature of incubation can be variable and depend i.a. on the subject that is to be treated.

A further object of the present invention are pharmaceutical preparations which comprise a therapeutically effective amount of RNAi molecules and/or expression vectors as defined herein and a pharmaceutically acceptable carrier, i.e. one or more pharmaceutically acceptable carrier substances and/or additives.

The term "therapeutically effective amount" as used herein means that amount of RNAi molecule(s) and/or expression vector(s) that elicits the biological or medicinal response in a tissue, system, animal or human that is being sought by a researcher, veterinarian, medical doctor or other clinician.

In another embodiment, the invention therefore relates to a pharmaceutical composition for the treatment of cancer, preferably glioma (preferably of glioblastoma), pancreatic cancer, head and neck cancer, melanoma, non-small-cell lung cancer or non-Hodgkin's lymphoma, comprising an RNAi molecule and/or expression vector according to the invention, and a pharmaceutically acceptable carrier. In yet another embodiment the invention relates to a pharmaceutical composition for the delay of progression of cancer, preferably glioma (preferably of glioblastoma), pancreatic cancer, head and neck cancer, melanoma, non-small-cell lung cancer or non-Hodgkin's lymphoma, comprising an RNAi molecule and/or expression vector according to the invention, and a pharmaceutically acceptable carrier.

The pharmaceutical composition according to the invention may further comprise at least one active compound, as defined above.

The pharmaceutical composition according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods.

The preparation of the pharmaceutical compositions can be carried out in a manner known per se. To this end, the nucleic acid and/or the active compound, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human medicine. For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiological sodium chloride solution, alcohols such as ethanol, glycerol, polyols, sucrose, invert sugar, glucose, mannitol, vegetable oils, etc. It is also possible to lyophilize the nucleic acid and/or the active compound and to use the resulting lyophilisates, for example, for preparing preparations for injection or infusion. Suitable carriers for microcapsules, implants or rods are, for example, copolymers of glycolic acid and lactic acid.

The pharmaceutical preparations can also contain additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

Preferably, the present composition is administered in a GLP/GMP solvent, containing or not cyclobetadextrine and/or similar compounds.

The dosage or amount of an RNAi molecule and/or expression vector used, in combination with one or more active compounds to be administered, depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to the nucleic acid and/or RNAi molecule and/or expression vector.

In a particularly preferred embodiment, the pharmaceutical composition according to the invention is injectable and is administered parenterally. The composition may for instance be administered by means of a standard Ommaya reservoir (micropumps) used to administrate drugs in patients with brain pathologies. These micropumps are placed subcutaneously (in the neck) by the time of the neurosurgical resection of the glioma, Such micropumps enable the delivery of the product (RNAi molecule(s), vector(s) or pharmaceutical composition(s) as defined herein) to the tumor cells. The delivered compounds, e.g. RNAi molecule(s), vector(s) or pharmaceutical composition(s) as defined herein, is preferably injected one or two times a week during months, or even years. The micropump can be replaced in case of technical problems.

Delivery using reservoirs, such as the above Ommaya reservoir (micropumps) is also applicable to deliver the product (RNAi molecule(s), vector(s) or pharmaceutical composition(s) as defined herein) to the tumor in cells in cancer types, in particular, glioma, non-Hodgkin's lymphomas, melanomas, pancreas cancers, head and neck cancers, and non-small-cell-lung cancers. For example, micropumps with intravenous catheters can deliver the product (RNAi molecule(s), vector(s) or pharmaceutical composition(s) as defined herein) into a patient, e.g., into the blood stream of a patient, alone or in addition with other therapies, such as chemotherapy, radiotherapy, immunotherapy, etc.

In another embodiment, the invention provides a kit comprising a pharmaceutical composition according to the invention, and an active compound as defined herein, for simultaneous, separate or sequential administration to a subject in need thereof.

Therapeutic Methods

Without being limited to any theory, the present inventors contemplate that the therapeutic benefits of knocking-down and thus significantly reducing galectin-1 expression in tumor cells may be mediated as follows:

Decrease the levels of migration of cancer cells, thus to delay the formation of metastases, or to delay the locoregional process of cancer invasion into adjacent healthy tissues (e.g., the brain in the case of glioma), given that galectin-1 is directly implicated in the cell migration features and/or metastatic processes in cancer, in particular in glioma, pancreatic cancer, head and neck cancer, melanoma, non-small-cell lung cancer and non-Hodgkin's lymphoma;

Increase the sensitivity to pro-apoptotic agents in these migratory-restricted cancer cells because (a) migrating cancer cells are often resistant to apoptosis, (b) cancer cells in which migration is restricted can become sensitive to apoptosis, and thus to pro-apoptotic agents, (c) most drugs used today to combat the above cancer types are pro-apoptotic drugs; thus, in addition to a direct therapeutical benefit of knocking-down galectin-1 in tumor cells of cancer patients (see above), the present invention also contemplates the combined use of chemotherapy and/or radiotherapy together with the anti-galectin-1 approach;

Decrease the capability of tumor cells to defend themselves against the attacks of the immune system because galectin-1 secreted by tumor cells induce dramatic cell death processes in those activated T cells which are bound to destroy cancer cells; thus, in addition to a direct therapeutical benefit of knocking-down galectin-1 in tumor cells of cancer patients (see above), the invention also contemplates the combined use of immunotherapy (using for example activated T cells) and/or gene therapy (using the targeted transfection of galectin-1 cell death receptor (CD3, CD7, CD45, CD95 for example) into human tumor cells) in addition to the anti-galectin-1 knocking-down approach.

For example, the therapeutic benefits of knocking-down and thus significantly reducing galectin-1 expression in tumor astrocytes are as follows.

Galectin-1 is involved in the migratory properties of malignant glioma, at least at three distinct levels, i.e.

tumor astrocyte adhesion, by modulating the levels of expression of integrin α9β1 and ADAM15, tumor astrocyte motility, by modifying the organization of the actin cytoskeleton through modifications in RhoA expression (Camby et al. 2002), and tumor astrocyte invasion, by modifying the levels of expression and secretion of MMP-2

Knocking-down galectin-1 expression in human glioma cells permits to reduce the invasion of the tumor astrocytes into the brain of the patients, and therefore enables the delay of the progression of the disease with an increase in the survival periods of the patients.

In addition, galectin-1 directly activates the migration properties of glioma cells (Camby et al. 2001, Rorive et al. 2001, Rao 2003) and clinical and experimental data demonstrate that intracellular signaling pathways involved in migratory glioma cells confer them the acquisition of resistance to apoptosis, thus to chemotherapy- and radiotherapy-induced apoptosis. It was demonstrated that reducing the levels of migration of tumor astrocytes increases the sensitivity of experimental gliomas to pro-apoptotic agents such as temozolomide (Lefranc et al., 2005b). Thus, reducing the migratory capabilities of tumor astrocytes in human gliomas decreases the levels of migration of tumor astrocytes into the brain parenchyma, a feature that in turn will decrease the resistance of tumor astrocytes to pro-apoptotic agents, a new feature that will in turn restore an increased sensitivity of tumor agents to pro-apoptotic agents such as temozolomide. Thus, in addition to a direct therapeutical benefit of knocking-down galectin-1 in tumor astrocytes of glioma patients (see above), we also claim the combined use of chemotherapy (as the one relating on the use of temozolomide or the PCV combination) and/or radiotherapy with our anti-galectin-1 approach.

In addition, galectin-1 secreted by tumor cells is a potent immunodulator that induces cell death of T-lymphocytes and thus favors tumor-immune escape (Rubinstein et al. 2004, Lui et al. 2005). Thus, knocking-down galectin-1 expression by glioma cells will reduce the release of galectin-1 in the tissue surrounding the glioma, so favoring T-cells immune response against the tumor. Thus, in addition to a direct therapeutical benefit of knocking-down galectin-1 in tumor astrocytes of glioma patients (see point 1), we also claim for the combined use of immunotherapy (using for example activated T cells) and/or gene therapy (using the targeted transfection of galectin-1 cell death receptor (CD3, CD7, CD45, CD95 for example) into human tumor astrocytes) in addition to our anti-galectin-1 knocking-down approach for treating human gliomas.

In view of the above, the invention provides a method for treating cancer, preferably glioma (preferably glioblastoma), pancreatic cancer, head and neck cancer, melanoma, non-small-cell lung cancer or non-Hodgkin's lymphoma, in a subject comprising administering an RNAi molecule, a vector or a composition as defined herein to said subject. In another embodiment, the invention relates to a method for delaying the progression of cancer, preferably glioma (preferably of glioblastoma), pancreatic cancer, head and neck cancer, melanoma, non-small-cell lung cancer or non-Hodgkin's lymphoma, in a subject comprising administering an RNAi molecule, a vector or a composition as defined herein to said subject. The term "subject" as used herein preferably refers to a human, but veterinary applications are also in the scope of the present invention targeting for example domestic livestock, laboratory or pet animals.

In view of the above, the invention further provides a method for down-regulating galectin-1 expression and comprising administering an RNAi molecule, a vector or a composition as defined herein.

The term "down-regulating galectin-1 expression", as used herein, refers to decrease galectin-1 (post-transcriptional) expression preferably by more than 50%, and more preferably by more than 70%, and even more preferably by more than 90%.

In another embodiment the invention relates to a method for reducing the migration of tumor cells, preferably cells of glioma (preferably of glioblastoma), pancreatic cancer, head and neck cancer, melanoma, non-small-cell lung cancer or non-Hodgkin's lymphoma, comprising administering an RNAi molecule, a vector or a composition as defined herein.

The term "reducing the migration of tumor cells", as used herein, refers to reduction in the number of migrating tumor cells preferably by more than 30%, and more preferably by more than 50%, and even more preferably by more than 70%.

In yet another embodiment, the invention relates to a method for reducing the resistance of tumor cells, preferably cells of glioma (preferably of glioblastoma), pancreatic cancer, head and neck cancer, melanoma, non-small-cell lung cancer or non-Hodgkin's lymphoma, to apoptosis comprising administering an RNAi molecule, a vector or a composition as defined herein.

The term "reducing the resistance of tumor cells to apoptosis", as used herein, refers to reduction in the number of tumor cells which are resistant to apoptosis preferably by more than 30%, and more preferably by more than 50%, and even more preferably by more than 70%.

The invention further provides a method for enhancing the efficacy of cancer therapies for the treatment of cancer, preferably glioma (preferably glioblastoma), pancreatic cancer, head and neck cancer, melanoma, non-small-cell lung cancer or non-Hodgkin's lymphoma, selected from the group comprising chemotherapy, radiation therapy, immunotherapy, and/or gene therapy comprising: administering an RNAi molecule, a vector or a composition as defined herein, and simultaneously, separately or sequentially administrating said cancer therapy.

The term "enhancing the efficacy of a cancer therapy", as used herein, refers to an improvement of conventional cancer treatments and includes reduction of the amount of the anti-cancer composition which is applied during the conventional cancer treatment, e.g. amount of radiation in radiotherapy, of chemotherapeutics in chemotherapy, of immunotherapeutics in immunotherapy or of vectors in gene based therapies, and/or to an increase in efficacy of the conventional therapy and the anti-cancer composition when applied at conventional doses or amounts during the conventional cancer therapy.

The reduction of the doses of radiations and chemotherapeutics applied during cancer therapy has several advantages. A reduction of the use of expensive anti-cancer compositions such as radiation or chemotherapeutics is not only cost-effective, but also allows reducing the toxicity of the applied compositions and the side-effects related thereto in the patient. Also, in general, an increase in the efficacy of the anti-cancer compositions applied at conventional doses enables to reduce the duration and the number of repetition of the conventional cancer therapy, which is also cost-effective and advantageous from a patient's point of view as to reduce toxicity and side-effect problems.

In summary, the present invention, relates to the use of an anti-galectin-1 therapeutic approach to combat human cancers in general, and malignant human gliomas, pancreatic cancer, head and neck cancer, melanoma, non-small-cell lung cancer and non-Hodgkin's lymphoma in particular. The present therapeutic approach is based on the use of anti-galectin-1 tools relating to RNA interference-(RNAi), anti-sense-, viral-vector-, or any other related approaches aiming to knock-down galectin-1 expression in human tumor cells.

The technical feasibility of the present approach is further illustrated by means of the following non-limitative examples wherein is demonstrated:
(I) the use of siRNA (or shRNA) to knock-down galectin-1 expression in tumor astrocytes (example 1),
(II) examples of types of vectors that can be used to deliver these siRNA (or shRNA) in tumor astrocytes, (example 2), and
(III) therapeutic protocols based on the use of clinically relevant in vivo models to deliver the present anti-galectin-1-based therapeutic approach in glioma patients (example 3).

EXAMPLES

Example 1

Examples of siRNA Sequences Targeted Against Galectin-1

Three sequences of human galectin 1 (from GenBank) were compared, including the sequence having accession number BC020675 (FIG. 1), BC001693 (FIG. 2) and NM_002305 (FIG. 3). Besides differences in length, NM_002305 differs from the two other sequences at 2 positions: an insertion of a C at position 19 and absence of a T at position 524. These differences have no consequences for the identification of RNAi molecules in accordance with the present invention. 33 "AA" doublets could be found in the representative sequence from BC020675 (SEQ ID NO: 67), as underlined in the sequence of FIG. 1.

Based on these sequences 33 putative DNA nucleid acids suitable for preparing siRNA sequences of human galectin-1 were identified and defined as SEQ NOs: 70-101; including:

| | |
|---|---|
| aaatcagccagcccatggccc, | (SEQ ID NO: 70) |
| aagctgccagatggatacgaa, | (SEQ ID NO: 71) |
| aaagacagcaacaacctgtgc, | (SEQ ID NO: 72) |
| aagtgttgcagaggtgtgcat, | (SEQ ID NO: 73) |
| aacatcctcctggactcaatc, | (SEQ ID NO: 74) |
| aatcatggcttgtggtctggt, | (SEQ ID NO: 75) |
| aacctgaatctcaaacctgga, | (SEQ ID NO: 76) |
| aatctcaaacctggagagtgc, | (SEQ ID NO: 77) |
| aaacctggagagtgccttcga, | (SEQ ID NO: 78) |
| aacctggagagtgccttcgag, | (SEQ ID NO: 79) |
| aagagcttcgtgctgaacctg, | (SEQ ID NO: 80) |
| aacctgggcaaagacagcaac, | (SEQ ID NO: 81) |
| aagacagcaacaacctgtgcc, | (SEQ ID NO: 82) |
| aacaacctgtgcctgcacttc, | (SEQ ID NO: 83) |
| aacctgtgcctgcacttcaac, | (SEQ ID NO: 84) |
| aaccctcgcttcaacgcccac, | (SEQ ID NO: 85) |
| aacgcccacggcgacgccaac, | (SEQ ID NO: 86) |
| aacaccatcgtgtgcaacagc, | (SEQ ID NO: 87) |
| aacagcaaggacggcggggcc, | (SEQ ID NO: 88) |

-continued

| | |
|---|---|
| aaggacggcggggcctggggg, | (SEQ ID NO: 89) |
| aacctgaccgtcaagctgcca, | (SEQ ID NO: 90) |
| aattcaagttccccaaccgcc, | (SEQ ID NO: 91) |
| aagttccccaaccgcctcaac, | (SEQ ID NO: 92) |
| aaccgcctcaacctggaggcc, | (SEQ ID NO: 93) |
| aacctggaggccatcaactac, | (SEQ ID NO: 94) |
| aactacatggcagctgacggt, | (SEQ ID NO: 95) |
| aagatcaaatgtgtggccttt, | (SEQ ID NO: 96) |
| aaatgtgtggcctttgactga, | (SEQ ID NO: 97) |
| aatgtgtggcctttgactgaa, | (SEQ ID NO: 98) |
| aatcagccagcccatggcccc, | (SEQ ID NO: 99) |
| aataaaggcagctgcctctgc, | (SEQ ID NO: 100) |
| aaaggcagctgcctctgctcc, | (SEQ ID NO: 101) |
| aaggcagctgcctctgctccc. | (SEQ ID NO: 102) |

Sequences having SEQ ID NOs: 71, 72 and 73 were further tested. FIG. 3 illustrates the position of SEQ ID NOs: 71 (underline), 72 (bold) and 73 (bold and underlined) sequences on the sequence of the human galectin-1 mRNA (accession number NM_002305).

On the basis of the sequences described above, the sequence of two siRNA that were used in this example to transfect cells are represented in FIG. 4, and named as siRNA-1 and siRNA-3.

Figure 5B:
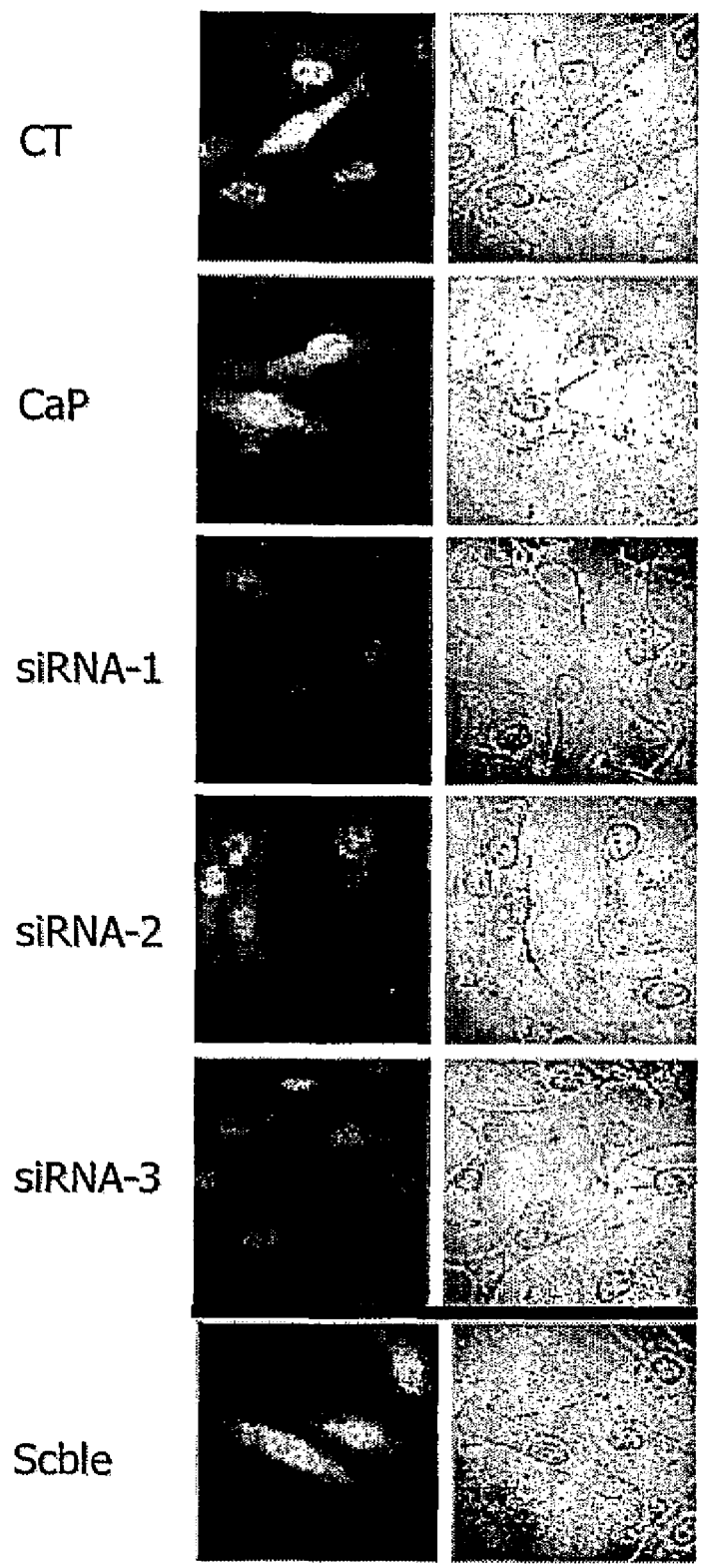

After the transfection (with calcium phosphate, CaP) of these sequences in three in vitro models of malignant glioma, i.e. U87, U373, Hs683, the protein expression of galectin-1 was checked both by Western blot and immunocytochemical fluorescent stainings. Results hereof are illustrated in FIG. 5. Green fluorescence reveals the specific immunocytochemical expression of galectin-1. These results show a 90% decreased expression of galectin-1 in siRNA-1 transfected cells as compared to controls, i. e. not transfected (CT), treated with CaP alone (CaP) or transfected with a scramble siRNA (Scrb). A similar, but less dramatic, decrease of galectin-1 expression was also observed after transfection with the siRNA-3. The scramble control condition is a non specific scramble sequence of siRNA-1. The absence of specificity of this sequence for any known human mRNA was checked by a BLAST alignment.

Example 2

Examples of shRNA Molecules According to the Invention

In this example, anti-galectin-1 shRNA sequences were cloned in the plasmid vector described and published by Dr. D. Takai (Department of Respiratory Medicine, University of Tokyo, Japan, Matsukura et al. 2003).

The shRNA expression vectors were constructed based on the siRNA-1 and siRNA-3 sequences as described above. Nucleotides sequences have been added upstream and downstream to the siRNA sequence for cloning purposes and shRNA expression. The end products obtained in the cytoplasm of cells by means of such type of constructs are similar to the sequences of siRNA-1 and siRNA-3. The sequences inserted in the plasmid vectors were checked by sequencing parts of the plasmids.

Figure 6:
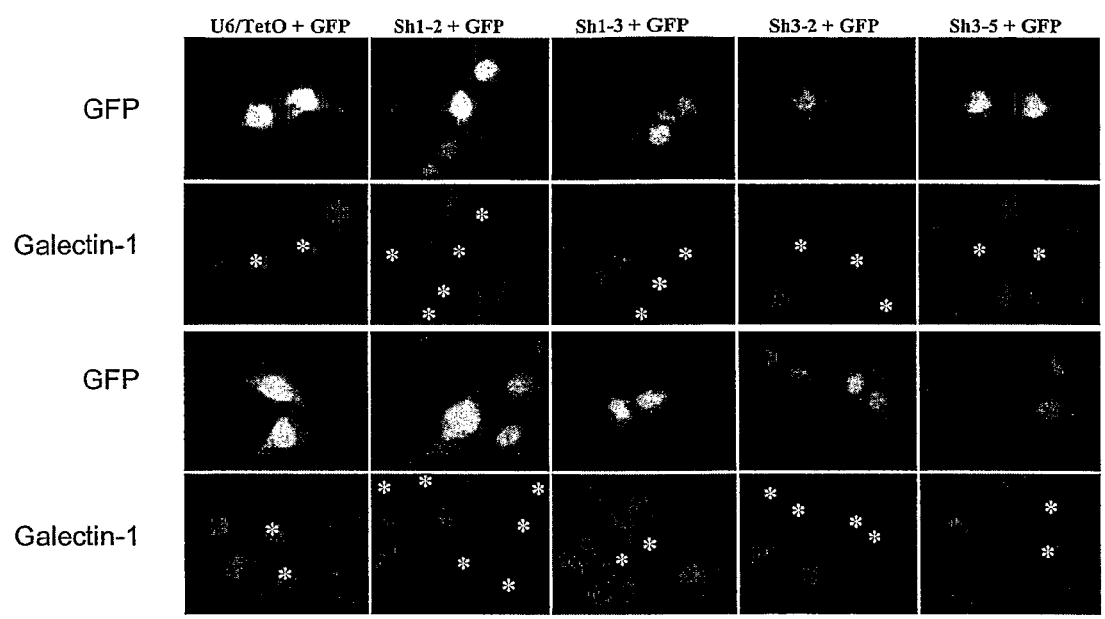
FIG. 6 shows galectin-1 expression in the cells transfected with an RNAi expression vector according to the invention. Co-transfected cells are marked with (*) for easy identification. Red fluorescence shows the immunocytochemical expression of galectin-1. U6TetO is an empty vector. Four shRNA constructs were tested. The vectors sh1-2 and sh1-3 on one hand, and sh3-2 and sh3-5 on the other hand are plasmids that contain the sequences with SEQ ID NOs 35 and 37, respectively, allowing expression of shRNA molecules that will generate siRNA molecules similar to siRNA-1 and siRNA-3 respectively.

These vectors were co-transfected with a GFP reporter vector coding for the green fluorescent protein in the U373 glioblastoma model. Galectin-1 expression in these cells was detected by fluorescent immunocytochemistry. The results are illustrated in the FIG. 6. Cells that incorporated the plasmid vectors (as revealed by the green fluorescence) are characterized by a significant reduced expression of galectin-1 (as specifically revealed with a red fluorochrome) as compared to controls and to adjacent non-transfected cells. Transfection with the vectors coding for the siRNA-1 were the most efficient.

Example 3

In Vivo Experimental Delivery of Anti-galectin-1-based RNAi Molecules

To prove that the in vivo delivery RNAi-related compounds against galectin-1 may be beneficial for patients with malignant gliomas, clinically relevant experimental models are needed. These models have been developed and concern the orthotopic graft of malignant rat or human glioma in the brain of conventional or nude mice or rats (Lefranc et al. 2002; Branle et al. 2002, Lefranc et al. 2003, Lefranc et al. 2004).

The clinical practice for glioma is usually a surgical resection of the tumor mass followed by adjuvant therapeutics that tend to combat the remaining infiltrative and migrating cells, responsible of the very pejorative prognosis of these tumors. To be as close as possible to the clinical practice of glioma, the glioma developing into the brain of mice or rats because of the orthotopic grafts of glioma cells is surgically resected and adjuvant experimental RNAi treatment is administrated either by systemic injection or directly at the site of surgery by means of micropump delivering the RNAi-related compound at the surgical site though a catheter. As in clinic the experimental treatment is thus administrated to the post-surgery remaining infiltrative malignant tumoral cells (Lefranc et al. 2002; Branle et al. 2002, Lefranc et al. 2003, Lefranc et al. 2004).

Example 4

In Vivo Experimental Delivery of Anti-galectin-1-based RNAi Molecules

Figure 7:
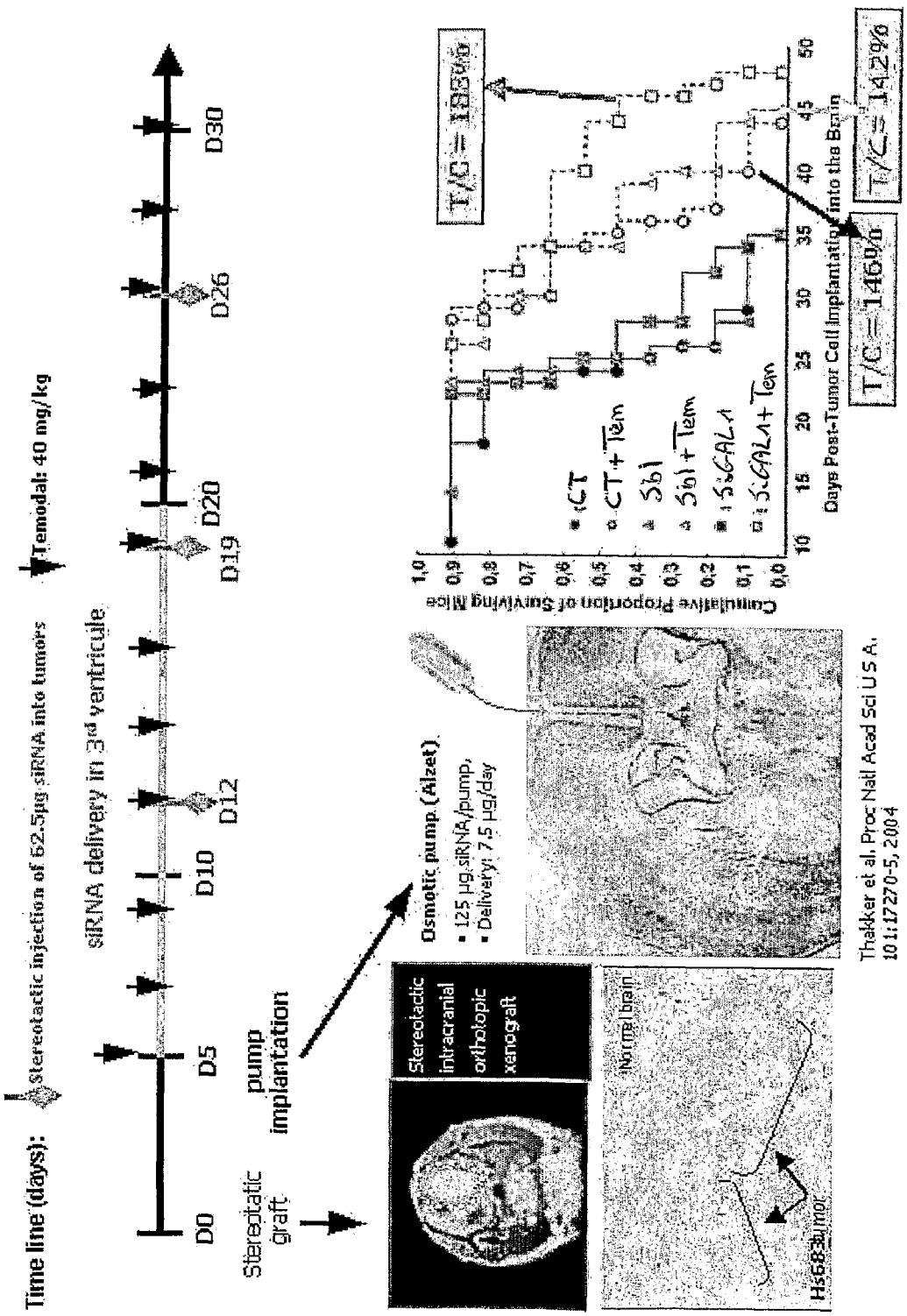
FIG. 7 shows in vivo delivery of antigalectin-1 siRNA for the treatment of experimental glioma.

Exemplary in vivo delivery of anti-galectin-1 siRNA SEQ ID NO:2 (siRNA-1) for the treatment of experimental glioma is shown in FIG. 7. This example show how the siRNA can be used in vivo when embedded in a micro-pump and delivered into the third ventricle of the brain to combat those migrating glioma cells that escape from the tumor bulk and that will escape surgery de-bulking.

Hs683 glioma cells were stereotactically grafted into the brain of nude mice. At day 5 post-graft a micro-pump containing the siRNA was subcutaneously implanted with its catheter delivering the siRNA into the $3^{rd}$ brain ventricle. At days 12, 19 and 26 post graft a stereotactic injection of siRNA into the tumor was performed (diamonds on the time line). Some animals also received Temodal (temozolomide) i.v. injections (arrows on the time line, open symbols for the survival curve). Mice bearing intracranial graft and treated with the combined administration of antigalectin-1 siRNA and Temodal survived to their tumor significantly longer than controls (T/C index: 183%). (CT, closed circles–control;

CT+Tem, open circles, control with Temodal; Sbl, closed triangles, scrambled siRNA; Sbl+Tem, open triangles, scrambled siRNA with Temodal; SiGal1, closed squared, anti-galectin-1 siRNA; SiGal1+Tem, open squares, anti-galectin-1 siRNA with Temodal).

An equivalent approach can be applied to clinically treat cancer patients with anti-galectin-1 RNAi, such as siRNA, of the present invention, in particular for glioma, non-Hodgkin's lymphomas, melanomas, pancreas cancers, head and neck cancers and non-small-cell-lung cancers. Such approach can thus use micro-pumps with intravenous catheters delivering the anti-galectin-1 RNAi into the patient, e.g., the blood stream of the patient, e.g., during the chemotherapy procedure.

REFERENCES

Benny O, Duvshani-Eshet M, Cargioli T, Bello L, Bikfalvi A, Carroll R S, Machluf M. Continuous delivery of endogenous inhibitors from poly(lactic-co-glycolic acid) polymeric microspheres inhibits glioma tumor growth. Clinical Cancer Research 11:768-776, 2005.

Berberat P O, Friess H, Wang L, Zhu Z, Bley T, Frigeri L, Zimmermann A, Buchler M W. Comparative analysis of galectins in primary tumors and tumor metastasis in human pancreatic cancer. J Histochem Cytochem 49: 539-549, 2001.

Branle F, Lefranc F, Camby I, Jeuken J, Geurts-Moespot S, Sprenger S, Sweep F, Kiss R, Salmon I. Evaluation of the efficiency of chemotherapy in in vivo orthotopic models of human glioma cells with and without 1p19q deletions and in C6 rat orthotopic allografts serving for the evaluation of surgery combined with chemotherapy. Cancer 95:641-655, 2002.

Camby I, Belot N, Lefranc F, Sadeghi N, de Launoit Y, Kaltner H, Musette S, Darro F, Danguy A, Salmon I, Gabius H J, Kiss R. Galectin-1 modulates human glioblastoma cell migration into the brain though modifications to the actin cytoskeleton and the levels of expression of small GTPases. J Neuropathol Exp Neurol 61: 585-596, 2002.

Camby I, Belot B, Rorive S, Lefranc F, Maurage C A, Lahm A, Kaltner H, Hadari Y, Ruchoux M M, Brotchi J, Zick Y, Salmon I, Gabius H J, Kiss R. Galectins are differentially expressed in supratentorial pilocytic astrocytomas, astrocytomas, anaplastic astrocytomas and glioblastomas, and significantly modulate tumor astrocyte migration. Brain Pathol 11: 12-26, 2001.

Choufani G, Nagy N, Saussez S, Marchant H, Bisschop P, Burchert M, Danguy A, Louryan S, Salmon I, Gabius H J, Kiss R, Hassid S. The levels of expression of galectin-1, galectin-3, and the Thomsen-Friedenreich antigen and their binding sites decrease as clinical aggressiveness increases in head and neck cancers. Cancer 86: 2353-2363, 1999.

Czauderna F, Fechtner M, Dames S, Aygun H, Klippel A, Pronk G J, Giese K, Kaufmann J. Structural variations and stabilizing modifications in an siRNA. Nucleic Acid Research 31: 2705-2716, 2003.

Danguy A, Camby I, Kiss R. Galectins and cancer. Biochim Biophys Acta 1572:285-293, 2002.

D'Haene N, Maris C, Sandras F, Dehou M F, Remmelink M, Decaestecker C, Salmon I. The differential expression of Galectin-1 and Galectin-3 in normal lymphoid tissue and non-Hodgkin's and Hodgkin's lymphomas. Int J Immunopathol Pharmacol 18: 431-443, 2005.

Dykxhoorn D M, Novina C D, Sharp P A. Killing the messenger: short RNAs that silence gene expression. Nat Rev Mol Cell Biol 4:457-467, 2003.

Elmen J, Thonberg H, Ljungberg K, Frieden M, Westergaard M, Xu Y, Wahren B, Liang Z, Orum H, Koch T, Wahlestedt C. Locked nucleic acid (LNA) mediated improvements in siRNA stability and functionality. Nucleic Acid Research 33:439-447, 2005.

Fitzner B, Walzel H, Sparmann G, Emmrich J, Liebe S, Jaster R. Galectin-1 is an inductor of pancreatic stellate cell activation. Cell Signal 17: 1240-1247, 2005.

Gabius H J, Andre S, Gunsenhauser I, Kaltner H, Kayser G, Kopitz J, Lahm H, Harms D, Szymas J, Kayser K. Association of galectin-1- but not galectin-3-dependent parameters with proliferation activity in human neuroblastomas and small cell lung carcinomas. Anticancer Res 22: 405-410, 2002.

Gillenwater A, Xu X C, el-Naggar A K, Clayman G L, Lotan R. Expression of galectins in head and neck squamous cell carcinoma. Head Neck 18: 422-432, 1996.

Grutzmann R, Pilarsky C, Ammerpohl O, Luttges J, Bohme A, Sipos B, Foerder M, Alldinger I, Jahnke B, Schackert H K, Kalthoff H, Kremer B, Kloppel G, Saeger H D. Gene expression profiling of microdissected pancreatic ductal carcinomas using high-density DNA microarrays. Neoplasia 6: 611-622, 2004.

Gunnersen J M, Spirkosa V, Smith P E, Danks R A, Tan S S. Growth and migration markers of rat C6 glioma cells identified by serial analysis of gene expression. Glia 32:146-154, 2000.

Harborth J, Elbashir S M, Vandenburgh K, Manninga H, Scaringe S A, Weber K, Tuschl T. Sequence, chemical, and structural variation of small interfering RNAs and short hairpin RNAs and the effect on mammalian gene silencing. Antisense Nucleic Acid Drug Dev 13: 83-105, 2003.

Kawakami K, Kawakami M, Kioi M, Hussain S R, Puri R K. Distribution kinetics of targeted cytotoxin in glioma by bolus or convection-enhanced delivery in a murine model. J Neurosurg 101:1004-1011, 2004.

Kleihues P, Cavenee W K: Pathology and genetics of tumours of the nervous system. International Agency for Research on Cancer (IARC) and WHO Health Organisation: Oxford, UK: Oxford Press, 2000.

Lefranc F, Brotchi J, Kiss R. Possible future issues in the treatment of glioblastomas: Special emphasis on cell migration and the resistance of migrating glioblastoma cells to apoptosis. J Clin Oncol 23:2411-2422, 2005a.

Lefranc F, Camby I, Belot N, Bruyneel E, Mareel M, Brotchi J, Salmon I, Kiss R. Gastrin significantly modifies the migratory abilities of experimental malignant astrocytic tumors. Lab Invest 82:1241-1252, 2002.

Lefranc F, James S, Camby I, Gaussin J F, Darro F, Brotchi J, Gabius H J, Kiss R. Combination of cimetidine and temozolomide induces significant increases in the survival periods of human U373 glioblastoma orthotopic xenograft-bearing nude mice as compared to tomozolomide alone. J Neurosurg, under press (April), 2005b.

Lefranc F, Mijatovic T, Mathieu V, Rorive S, Decaestecker C, Debeir O, Brotchi J, Van Ham Ph, Salmon I, Kiss R. Characterization of gastrin-induced proangiogenic effects in vivo in orthotopic U373 experimental human glioblastomas, and in vitro in Human Umbilical Vein Endothelial Cells (HUVECs). Clin Cancer Res 10: 8250-8265, 2004.

Lefranc F, Sadeghi N, Metens T, Brotchi J, Salmon I, Kiss R. Characterization of gastrin-induced cytostatic effect on cell proliferation in experimental malignant gliomas. Neurosurgery 52: 881-891, 2003.

Liu F T, Rabinovich G. Galectins as modulators of tumor progression. Nat Rev Cancer 5:29-41, 2005.

Matsukura S, Jones P A, Takai D. Establishment of conditionnal vectors for hairpin siRNA knockdown. Nucleic Acid Research 31e77, 2003.

Menei P, Benoit J P. Implantable drug-releasing biodegradable microspheres for local treatment of brain glioma. Acta Neurochir 88:51-55, 2003.

Morrissey D V, Lockridge J A, Shaw L, Blanchard K, Jensen K, Breen W, Hartsough K, Machemer L, Radka S, Jadhav V, Vaish N, Zinnen S, Vargeese C, Bowman K, Shaffer C S, Jeffs L B, Judge A, MacLachlan I, Polisky B. Potent and persistent in vivo anti-HBV activity of chemically modified siRNAs. *Nat Biotechnol* 23:1002-7, 2005.

Rao J S. Molecular mechanisms of glioma invasiveness: the role of proteases. Nat Rev Cancer 3:489-501, 2003.

Rorive S, Belot N, Decaestecker C, Lefranc F, Gordower L, Micik S, Maurage C A, Kaltner H, Ruchoux M M, Danguy A, Gabius H J, Salmon I, Kiss R, Camby I. Galectin-1 is highly expressed in human gliomas with relevance for modulation of invasion of tumor astrocytes into the brain parenchyma. Glia 33: 241-255, 2001; Erratum: Glia 33: 166.

Rabinovich G A, Rubinstein N, Matar P, Rozados V, Gervasoni S, Scharovsky G O. The antimetastatic effect of a single low dose of cyclophosphamide involves modulation of galectin-1 and Bcl-2 expression. Cancer Immunol Immunother 50: 597-603, 2002.

Rubinstein N, Alvarez M, Zwirner N W, Toscano M A, Ilarregui J M, Bravo A, Mordoh J, Fainboim L, Podhajcer O L, Rabinovich G A. Targeted inhibition of galectin-1 gene expression in tumor cells results in heightened T cell-mediated rejection; A potential mechanism of tumor-immune privilege. *Cancer Cell* 5: 241-251, 2004.

Schiffelers R M, Ansari A, Xu J, Zhou O, Tang Q, Storm G, Molema G, Lu P Y, Scaria P V, Woodle M C. Cancer siRNA therapy by tumor selective delivery with ligand-targeted sterically stabilized nanoparticule. Nucleic Acid Research 32:e149-e158, 2004.

Shen J, Person M D, Zhu J, Abbruzzese J L, Li D. Protein expression profiles in pancreatic adenocarcinoma compared with normal pancreatic tissue and tissue affected by pancreatitis as detected by two-dimensional gel electrophoresis and mass spectrometry. Cancer Res 64: 9018-9026, 2004.

Shi N, Pardridge W M. Noninvasive gene targeting to the brain. Proc Natl Acad Sci USA 97:7567-7672, 2000.

Song E, Zhu P, Lee S K, Chowdhury D, Kussman S, Dykxhoorn D M, Feng Y, Palliser D, Weiner D B, Shankar P, Marasco W A, Lieberman J. Antibody mediated in vivo delivery of small interfering RNAs via cell-surface receptors. *Nat Biotechnol* 23:709-717, 2005.

Spankuch B, Matthess Y, Knecht R, Zimmer B, Kaufmann M, Strebhardt K. Cancer inhibition in nude mice after systemic application of U6 promoter-driven short hairpin RNAs against PLK1. J Natl Cancer Inst 96:862-872, 2004.

Szoke T, Kayser K, Baumhakel J D, Trojan I, Furak J, Tiszlavicz L, Horvath A, Szluha K, Gabius H J, Andre S. Prognostic significance of endogenous adhesion/growth-regulatory lectins in lung cancer. Oncology 69: 167-174, 2005.

Thakker D R, Natt F, Husken D, Maier R, Muller M, van der Putten H, Hoyer D, Cryan J F. Neurochemical and behavioral consequences of widespread gene knockdown in the adult mouse brain by using nonviral RNA interference. Proc Natl Acad Sci USA 101:17270-5, 2004.

Tinari N, Kuwabara I, Huflejt M E, Shen P F, Iacobelli S, Liu F T. Glycoprotein 90K/MAC-2BP interacts with galectin-1 and mediates galectin-1-induced cell aggregation. Int J Cancer 91: 167-172, 2001.

van den Brule F A, Buicu C, Baldet M, Sobel M E, Cooper D N, Marschal P, Castronovo V. Galectin-1 modulates human melanoma cell adhesion to laminin. Biochem Biophys Res Commun 209: 760-767, 1995.

Yamaoka K, Mishima K, Nagashima Y, Asai A, Sanai Y, Kirino T. Expression of galectin-1 mRNA with the malignant potential of human gliomas and expression of antisense galectin-1 inhibits the growth of 9 glioma cells. J Neurosci Res 59:722-30, 2000.

Zanetta J-P. Structure and functions of lectins in the central and peripheral nervous system. Acta Anat 161:180-195, 1998.

Zhang Y F, Bryant J, Charles A, Boado R J, Pardridge W M. Intravenous RNA interference gene therapy targeting the human epidermal growth factor receptor prolongs survival in intracranial brain cancer Clin Cancer Res 10:3667-3677, 2004.

Zhang W, Yang H, Kong X, Mohapatra S, San Juan-Vergara H, Hellermann G, Behera S, Singam R, Lockey R F, Mohapatra S S. Inhibition of respiratory syncytial virus infection with intranasal siRNA nanoparticles targeting the viral NS1 gene. Nat Med 11:56-62, 2005, Erratum in: Nat Med 11:233, 2005.

---

The invention claimed is:

1. A method of reducing the expression of galectin-1 in tumor cells comprising: providing an RNAi molecule of the sequences of SEQ ID NOs: 2, 3, 1, 5 to 18, 19, 20 to 25 or 27 to 33, or a fragment or derivative thereof showing at least 80% sequence identity to SEQ ID NOs: 2, 3, 1, 5 to 18, 20 to 25 or 27 to 33 or showing at least 85% sequence identity to SEQ ID NO: 19, to tumor cells, wherein the RNAi molecule is suitable for reducing the expression of galectin-1 in tumor cells.

2. A RNAi molecule suitable for reducing the expression of galectin-1 in tumor cells comprising any of the sequences of SEQ ID NOs: 2, 3, 1, 5 to 18, 19, 20 to 25 or 27 to 33, or a fragment or derivative thereof showing at least 80% sequence identity to SEQ ID NOs: 2, 3, 1, 5 to 18, 20 to 25 or 27 to 33 or showing at least 85% sequence identity to SEQ ID NO: 19.

3. A method of reducing the expression of galectin-1 in tumor cells comprising: providing to tumor cells a DNA molecule comprising any of the sequences of SEQ ID NOs: 35, 36, 34, 38 to 51, 52, 53 to 58 or 60 to 66, or a fragment or derivative thereof showing at least 80% sequence identity to SEQ ID NOs: 35, 36, 34, 38 to 51, 53 to 55 or 60 to 66 or showing at least 85% sequence identity to SEQ ID NO: 52, which encodes an RNAi molecule suitable for reducing the expression of galectin-1 in tumor cells.

4. The method of claim 3, wherein the DNA molecule is inserted in an expression vector suitable for the production of dsRNA.

5. An expression vector comprising the sequences of SEQ ID NOs: 35, 36, 34, 38 to 51, 52, 53 to 58 or 60 to 66, or a fragment or derivative thereof showing at least 80% sequence identity to SEQ ID NOs: 35, 36, 34, 38 to 51, 53 to 55 or 60 to 66 or showing at least 85% sequence identity to SEQ ID NO: 52.

6. A method of treating cancer comprising administering the RNAi molecule of claim 2 or a vector that encodes the RNAi molecule of claim 2 to a patient in need thereof.

7. A method of delaying the progression of cancer comprising administering the RNAi molecule of claim 2 or a vector that encodes the RNAi molecule of claim 2 to a patient in need thereof.

8. The method of claim 6, wherein the RNAi molecule and/or the vector are used in combination with any of the cancer therapies selected from the group comprising chemotherapy, radiation therapy, immunotherapy, and/or gene therapy.

9. The method of claim 6, wherein the RNAi molecule and/or the vector are used in combination with an active compound suitable for treating cancer.

10. A pharmaceutical composition for the treatment of cancer comprising an RNAi molecule as defined in claim 2 or a vector that encodes the RNAi molecule of claim 2, and a pharmaceutically acceptable carrier.

11. A kit comprising a pharmaceutical composition according to claim 10, and an active compound suitable for treating cancer and/or for delaying the progression thereof, for simultaneous, separate or sequential administration to a subject.

12. Method for treating cancer according to claim 6, wherein said cancer is selected from the group consisting of glioma, pancreatic cancer, head and neck cancer, melanoma, non-small-cell lung cancer or non-Hodgkin's lymphoma.

13. Method for delaying the progression of cancer according to claim 7, wherein said cancer is selected from the group consisting of glioma, pancreatic cancer, head and neck cancer, melanoma, non-small-cell lung cancer or non-Hodgkin's lymphoma.

14. Method for down-regulating galectin-1 expression in a tumor cell, comprising contacting the cell with an RNAi molecule as defined in claim 2, or a vector that encodes the RNAi molecule of claim 2.

15. Method for reducing the migration of tumor cells, comprising administering an RNAi molecule as defined in claim 2, or a vector that encodes the RNAi molecule of claim 2.

16. Method for reducing the resistance of tumor cells, an RNAi molecule as defined in claim 2, or a vector that encodes the RNAi molecule of claim 2.

17. Method for enhancing the efficacy of cancer therapies for the treatment of cancer, selected from the group comprising chemotherapy, radiation therapy, immunotherapy, and/or gene therapy comprising:
  administering an RNAi molecule as defined in claim 2, or a vector that encodes the RNAi molecule of claim 2, and simultaneously, separately or sequentially administrating said cancer therapy.

18. The method of claim 15, wherein the cancer is glioma, pancreatic cancer, head and neck cancer, melanoma, non-small- cell lung cancer or non-Hodgkin's lymphoma.

19. The method of claim 16, wherein the cancer is glioma, pancreatic cancer, head and neck cancer, melanoma, non-small- cell lung cancer or non-Hodgkin's lymphoma.

20. The method of claim 17, wherein the cancer is glioma, pancreatic cancer, head and neck cancer, melanoma, non-small- cell lung cancer or non-Hodgkin's lymphoma.

21. The method of claim 9, wherein the cancer is selected from the group consisting of glioma, pancreatic cancer, head and neck cancer, melanoma, non-small-cell lung and non-Hodgkin's lymphoma.

22. The method of claim 10, wherein the cancer is selected from the group consisting of glioma, pancreatic cancer, head and neck cancer, melanoma, non-small-cell lung and non-Hodgkin's lymphoma.

23. The method of claim 11, wherein the cancer is selected from the group consisting of glioma, pancreatic cancer, head and neck cancer, melanoma, non-small-cell lung and non-Hodgkin's lymphoma.

\* \* \* \* \*

UNITED STATES PATENT AND TRADEMARK OFFICE
CERTIFICATE OF CORRECTION

PATENT NO.        : 7,964,575 B2
APPLICATION NO.   : 11/911342
DATED             : June 21, 2011
INVENTOR(S)       : Camby et al.

It is certified that error appears in the above-identified patent and that said Letters Patent is hereby corrected as shown below:

Page 1, Column 2, Line 14, Other Publications "Nuclleic Acids" should be changed to --Nucleic Acids--

Page 1, Column 2, Line 31, Other Publications " "Galectin-I as a" should be changed to --"Galectin-1 as a--

Sheet 1 of 6, (FIG. 1), Line 1, "(galectin 1)," should be changed to --(galectin-1),--

Sheet 1 of 6, (FIG. 2), Line 1, "(galectin 1)," should be changed to --(galectin-1),--

Sheet 1 of 6, (FIG. 3), Line 1, "(galectin 1)," should be changed to --(galectin-1),--

Sheet 6 of 6, (FIG. 7), Line 5, "Stereotatic" should be changed to --Stereotactic--

Column 1, Line 41, "signaling pathways is" should be changed to --signaling pathways are--

Column 6, Line 12, "for simulatenous," should be changed to --for simultaneous,--

Column 7, Line 4, "1 (galectin 1)," should be changed to --1 (galectin-1),--

Column 7, Line 7, "1 (galectin 1)," should be changed to --1 (galectin-1),--

Column 7, Line 10, "1 (galectin 1)," should be changed to --1 (galectin-1),--

Column 11, Line 54, "-3'," should be changed to -- -3'--

Column 12, Line 49, "-3'," should be changed to -- -3'--

Column 12, Line 51, "-3'," should be changed to -- -3'--

Column 14, Line 11, "micropsheres," should be changed to --microspheres,--

Column 15, Line 42, "-3'," should be changed to -- -3'--

Column 16, Line 65, "derived form the" should be changed to --derived from the--

Column 21, Line 62, "of MMP-2" should be changed to --of MMP-2.--

Column 24, Line 20, "human galectin 1" should be changed to --human galectin-1--

Column 28, Line 56, "to tomozolomide alone." should be changed to --to temozolomide alone.--

Column 29, Lines 3-4, "of conditionnal vectors" should be changed to --of conditional vectors--

Signed and Sealed this
Thirteenth Day of December, 2011

David J. Kappos
*Director of the United States Patent and Trademark Office*

Column 29, Line 35, "Zhou O," should be changed to --Zhou Q,--

Column 63, Line 21, "small- cell lung" should be changed to --small-cell lung--

Column 64, Line 3, "small- cell lung" should be changed to --small-cell lung--

Column 64, Line 6, "small- cell lung" should be changed to --small-cell lung--